US009581526B2

(12) United States Patent
Arjavac et al.

(10) Patent No.: US 9,581,526 B2
(45) Date of Patent: *Feb. 28, 2017

(54) METHOD FOR S/TEM SAMPLE ANALYSIS

(71) Applicant: FEI Company, Hillsboro, OR (US)

(72) Inventors: Jason Arjavac, Hillsboro, OR (US); Pei Zou, Shanghai (CN); David James Tasker, Beaverton, OR (US); Maximus Theodorus Otten, Best (NL); Gerhard Daniel, Portland, OR (US)

(73) Assignee: FEI COMPANY, Hillsboro, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/047,064

(22) Filed: Feb. 18, 2016

(65) Prior Publication Data
US 2016/0163506 A1    Jun. 9, 2016

Related U.S. Application Data

(63) Continuation of application No. 14/546,244, filed on Nov. 18, 2014, now Pat. No. 9,275,831, which is a
(Continued)

(51) Int. Cl.
*G01N 1/28* (2006.01)
*G01N 1/06* (2006.01)
(Continued)

(52) U.S. Cl.
CPC ............... *G01N 1/28* (2013.01); *G01N 1/06* (2013.01); *G01N 1/08* (2013.01); *G01N 1/32* (2013.01);
(Continued)

(58) Field of Classification Search
CPC .. G01N 1/06; G01N 1/08; G01N 1/28; G01N 1/32; G01N 23/04
See application file for complete search history.

(56) References Cited

U.S. PATENT DOCUMENTS

| 5,254,438 A | 10/1993 | Owen et al. |
| 5,270,552 A * | 12/1993 | Ohnishi ............. G01N 23/2202 250/307 |

(Continued)

FOREIGN PATENT DOCUMENTS

| EP | 1696219 A1 | 8/2006 |
| JP | 60136315 | 7/1985 |

(Continued)

OTHER PUBLICATIONS

Potter, Clinton S., et al., "Robotic grid loading system for a transmission electron microscope," Journal of Structural Biology, 2004, pp. 431-440, vol. 146.

(Continued)

*Primary Examiner* — Jack Berman
(74) *Attorney, Agent, or Firm* — Scheinberg & Associates, P.C.; Michael O. Scheinberg

(57) ABSTRACT

An improved method and apparatus for S/TEM sample preparation and analysis. Preferred embodiments of the present invention provide improved methods for TEM sample creation, especially for small geometry (<100 nm thick) TEM lamellae. Preferred embodiments of the present invention also provide an in-line process for S/TEM based metrology on objects such as integrated circuits or other structures fabricated on semiconductor wafer by providing methods to partially or fully automate TEM sample creation, to make the process of creating and analyzing TEM samples less labor intensive, and to increase throughput and reproducibility of TEM analysis.

18 Claims, 24 Drawing Sheets

Related U.S. Application Data continuation of application No. 13/777,018, filed on Feb. 26, 2013, now Pat. No. 8,890,064, which is a continuation of application No. 12/446,387, filed as application No. PCT/US2007/082166 on Oct. 22, 2007, now Pat. No. 8,455,821.

(60) Provisional application No. 60/853,183, filed on Oct. 20, 2006.

(51) Int. Cl.

| | | |
|---|---|---|
| *G01N 1/08* | (2006.01) | |
| *G01N 23/04* | (2006.01) | |
| *G01N 1/32* | (2006.01) | |
| *H01J 37/305* | (2006.01) | |
| *H01J 37/26* | (2006.01) | |
| *H01J 37/06* | (2006.01) | |
| *H01J 37/18* | (2006.01) | |
| *H01J 37/20* | (2006.01) | |
| *H01J 37/28* | (2006.01) | |

(52) U.S. Cl.
CPC .............. *G01N 23/04* (2013.01); *H01J 37/06* (2013.01); *H01J 37/18* (2013.01); *H01J 37/20* (2013.01); *H01J 37/26* (2013.01); *H01J 37/28* (2013.01); *H01J 37/3056* (2013.01); *H01J 2237/063* (2013.01); *H01J 2237/182* (2013.01); *H01J 2237/204* (2013.01); *H01J 2237/208* (2013.01); *H01J 2237/2802* (2013.01); *H01J 2237/31745* (2013.01); *H01J 2237/31749* (2013.01)

(56) References Cited

U.S. PATENT DOCUMENTS

| | | | |
|---|---|---|---|
| 5,315,123 A | 5/1994 | Itoh et al. | |
| 5,656,811 A | 8/1997 | Itoh et al. | |
| 5,847,821 A | 12/1998 | Tracy et al. | |
| 5,923,020 A | 7/1999 | Kurokawa et al. | |
| 5,942,805 A | 8/1999 | Winer et al. | |
| 6,039,000 A | 3/2000 | Libby et al. | |
| 6,188,072 B1 | 2/2001 | Chung | |
| 6,300,626 B1 | 10/2001 | Brock et al. | |
| 6,300,628 B1 | 10/2001 | Fujii et al. | |
| 6,373,070 B1 | 4/2002 | Rasmussen | |
| 6,417,512 B1 | 7/2002 | Suzuki | |
| 6,420,722 B2 | 7/2002 | Moore et al. | |
| 6,497,194 B1 | 12/2002 | Libby et al. | |
| 6,521,890 B2 | 2/2003 | Ishitani et al. | |
| 6,527,967 B1 | 3/2003 | Suzuki | |
| 6,538,254 B1* | 3/2003 | Tomimatsu | H01J 37/3056 250/442.11 |
| 6,570,170 B2 | 5/2003 | Moore | |
| 6,573,516 B2 | 6/2003 | Kawakami | |
| 6,576,900 B2 | 6/2003 | Kelly et al. | |
| 6,593,583 B2 | 7/2003 | Iwasaki | |
| 6,608,920 B1 | 8/2003 | Su et al. | |
| 6,681,039 B1 | 1/2004 | Roberts et al. | |
| 6,700,121 B1 | 3/2004 | Kelly et al. | |
| 6,709,554 B2 | 3/2004 | Ferranti et al. | |
| 6,717,156 B2 | 4/2004 | Sugaya et al. | |
| 6,781,125 B2 | 8/2004 | Tokuda et al. | |
| 6,828,566 B2 | 12/2004 | Tomimatsu et al. | |
| 6,841,788 B1 | 1/2005 | Robinson et al. | |
| 6,842,538 B2 | 1/2005 | Lee et al. | |
| 6,871,114 B1 | 3/2005 | Green et al. | |
| 6,927,391 B2 | 8/2005 | Tokuda et al. | |
| 6,963,068 B2 | 11/2005 | Asselbergs et al. | |
| 6,965,895 B2 | 11/2005 | Smith et al. | |
| 6,982,429 B2 | 1/2006 | Robinson et al. | |
| 6,993,177 B1* | 1/2006 | Bachelder | G06K 9/6203 382/151 |
| 7,002,152 B2 | 2/2006 | Grunewald | |
| 7,005,636 B2 | 2/2006 | Tappel | |
| 7,034,316 B2 | 4/2006 | Wagner et al. | |
| 7,041,985 B1 | 5/2006 | Wang et al. | |
| 7,045,275 B2 | 5/2006 | Lee et al. | |
| 7,047,099 B2 | 5/2006 | Shanmugasundram et al. | |
| 7,069,101 B1 | 6/2006 | Arackaparambil et al. | |
| 7,071,475 B2 | 7/2006 | Tomimatsu et al. | |
| 7,095,024 B2 | 8/2006 | Adachi et al. | |
| 7,103,439 B1 | 9/2006 | Bode et al. | |
| 7,205,554 B2 | 4/2007 | Tokuda et al. | |
| 7,205,560 B2 | 4/2007 | Tokuda et al. | |
| 7,297,965 B2 | 11/2007 | Kidron et al. | |
| 7,348,556 B2 | 3/2008 | Chitturi et al. | |
| 7,381,971 B2 | 6/2008 | Moore et al. | |
| 7,408,178 B2 | 8/2008 | Tappel | |
| 7,414,252 B2 | 8/2008 | Moore et al. | |
| 7,423,263 B2 | 9/2008 | Hong et al. | |
| 7,442,924 B2 | 10/2008 | Giannuzzi et al. | |
| 7,465,945 B2 | 12/2008 | Tokuda et al. | |
| 7,470,918 B2 | 12/2008 | Tokuda et al. | |
| 7,511,282 B2 | 3/2009 | Agorio et al. | |
| 7,550,750 B2 | 6/2009 | Tokuda et al. | |
| 7,603,767 B2 | 10/2009 | Goko et al. | |
| 7,615,745 B2 | 11/2009 | Schampers et al. | |
| 7,700,367 B2 | 4/2010 | Fujii | |
| 7,880,151 B2 | 2/2011 | Wells | |
| 8,134,124 B2* | 3/2012 | Blackwood | G01N 1/32 250/304 |
| 8,455,821 B2* | 6/2013 | Arjavac | G01N 1/32 250/304 |
| 8,618,520 B2 | 12/2013 | Tokuda et al. | |
| 8,890,064 B2* | 11/2014 | Arjavac | G01N 1/32 250/304 |
| 9,275,831 B2* | 3/2016 | Arjavac | G01N 1/32 |
| 2002/0079463 A1 | 6/2002 | Shichi et al. | |
| 2002/0092985 A1 | 7/2002 | Ishitani et al. | |
| 2002/0164077 A1 | 11/2002 | Lee et al. | |
| 2002/0196536 A1 | 12/2002 | Ott | |
| 2003/0183776 A1 | 10/2003 | Tomimatsu et al. | |
| 2004/0245466 A1 | 12/2004 | Robinson et al. | |
| 2005/0010317 A1 | 1/2005 | Hadar et al. | |
| 2005/0079689 A1 | 4/2005 | Lim | |
| 2006/0017016 A1 | 1/2006 | Tappel | |
| 2006/0102608 A1 | 5/2006 | Katsuta et al. | |
| 2006/0284357 A1 | 12/2006 | Goko et al. | |
| 2007/0272854 A1 | 11/2007 | Agorio et al. | |
| 2008/0142711 A1 | 6/2008 | Lundquist | |
| 2010/0300873 A1 | 12/2010 | Blackwood et al. | |

FOREIGN PATENT DOCUMENTS

| | | |
|---|---|---|
| JP | 62174918 | 1/1989 |
| JP | H06342750 | 12/1994 |
| JP | H07333120 | 12/1995 |
| JP | 08005528 | 1/1996 |
| JP | H09306411 | 11/1997 |
| JP | H11108810 | 4/1999 |
| JP | H11183339 | 7/1999 |
| JP | 11265679 | 9/1999 |
| JP | H11330186 | 11/1999 |
| JP | 20000035390 A | 2/2000 |
| JP | 2000155081 A | 6/2000 |
| JP | 2000241319 A | 9/2000 |
| JP | 2000268768 A | 9/2000 |
| JP | 2001319954 A | 11/2001 |
| JP | 2002141382 A | 5/2002 |
| JP | 2002148159 A | 5/2002 |
| JP | 2003203959 A | 7/2003 |
| JP | 2004111097 A | 4/2004 |
| JP | 2004164966 A | 6/2004 |
| JP | 200420519 | 10/2004 |
| JP | 2005114578 A | 4/2005 |
| JP | 2006144825 A | 6/2006 |
| JP | 2008008850 A | 1/2008 |
| WO | WO9905506 A1 | 2/1999 |
| WO | WO0127967 A1 | 4/2001 |
| WO | WO02075806 A1 | 9/2002 |

(56) References Cited

FOREIGN PATENT DOCUMENTS

| WO | WO2008049133 A2 | 4/2008 |
| WO | WO2008051880 A2 | 5/2008 |
| WO | WO2008051937 A2 | 5/2008 |

OTHER PUBLICATIONS

Giannuzzi, Lucille A., et al., "FIB Lift-Out for Defect Analysis," Microelectronic Failure Analysis: Desk Reference, Nov. 2002, pp. 29-35.

Giannuzzi, Lucille A., et al., "FIB Lift-Out Specimen Preparation Techniques," Introduction to Focused Ion Beams, 2005, Chapter 10, pp. 201-228.

Langford, Richard M., "Focused Ion Beams Techniques for Nanomaterials Characterization," Microscopy Research and Technique, 2006, pp. 538-549, vol. 69.

Lee Jon C., et al., "The Versatile Application for In-Situ Lift-Out TEM Sample Preparation by Micromanipulator and Nanomotor," 31st International Symposium for Testing and Failure Analysis, San Jose, California, Nov. 2005.

Lensing, Kevin, et al., "Integrated Metrology and Wafer-Level Control," AMD Automated Precision, Jun. 1, 2006, 6 pgs.

Prenitzer, B.I., et al., "The Correlation between Ion Beam/Material Interactions and Practical FIB Specimen Preparation," Microsc. Microanal., 2003, pp. 216-236, vol. 9.

\* cited by examiner

METHOD FOR S/TEM SAMPLE ANALYSIS

The present application is a continuation of U.S. application Ser. No. 14/546,244, filed Nov. 18, 2014, which is a continuation of U.S. application Ser. No. 13/777,018, filed Feb. 26, 2013, which is a continuation of Ser. No. 12/446,387, filed Sep. 16, 2009, which is a 371 National Phase filing of PCT Application PCT/US2007/082166, filed Oct. 22, 2007, which claims priority from U.S. Prov. Pat. App. No. 60/853,183, filed Oct. 20, 2006, all of which are hereby incorporated by reference.

TECHNICAL FIELD OF THE INVENTION

The present invention relates to preparation of samples and methods of analysis for transmission electron microscopes and scanning transmission electron microscopes.

BACKGROUND OF THE INVENTION

Semiconductor manufacturing, such as the fabrication of integrated circuits, typically entails the use of photolithography. A semiconductor substrate on which circuits are being formed, usually a silicon wafer, is coated with a material, such as a photoresist, that changes solubility when exposed to radiation. A lithography tool, such as a mask or reticle, positioned between the radiation source and the semiconductor substrate casts a shadow to control which areas of the substrate are exposed to the radiation. After the exposure, the photoresist is removed from either the exposed or the unexposed areas, leaving a patterned layer of photoresist on the wafer that protects parts of the wafer during a subsequent etching or diffusion process.

The photolithography process allows multiple integrated circuit devices or electromechanical devices, often referred to as "chips," to be formed on each wafer. The wafer is then cut up into individual dies, each including a single integrated circuit device or electromechanical device. Ultimately, these dies are subjected to additional operations and packaged into individual integrated circuit chips or electromechanical devices.

During the manufacturing process, variations in exposure and focus require that the patterns developed by lithographic processes be continually monitored or measured to determine if the dimensions of the patterns are within acceptable ranges. The importance of such monitoring, often referred to as process control, increases considerably as pattern sizes become smaller, especially as minimum feature sizes approach the limits of resolution available by the lithographic process. In order to achieve ever-higher device density, smaller and smaller feature sizes are required. This may include the width and spacing of interconnecting lines, spacing and diameter of contact holes, and the surface geometry such as corners and edges of various features. Features on the wafer are three-dimensional structures and a complete characterization must describe not just a surface dimension, such as the top width of a line or trench, but a complete three-dimensional profile of the feature. Process engineers must be able to accurately measure the critical dimensions (CD) of such surface features to fine tune the fabrication process and assure a desired device geometry is obtained.

Typically, CD measurements are made using instruments such as a scanning electron microscope (SEM). In a scanning electron microscope (SEM), a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface. As features continue to get smaller and smaller, however, there comes a point where the features to be measured are too small for the resolution provided by an ordinary SEM.

Transmission electron microscopes (TEMs) allow observers to see extremely small features, on the order of nanometers. In contrast SEMs, which only image the surface of a material, TEM also allows analysis of the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite site. Samples, also referred to as lamellae, are typically less than 100 nm thick.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface.

Because a sample must be very thin for viewing with transmission electron microscopy (whether TEM or STEM), preparation of the sample can be delicate, time-consuming work. The term "TEM" as used herein refers to a TEM or an STEM and references to preparing a sample for a TEM are to be understood to also include preparing a sample for viewing on an STEM. The term "S/TEM" as used herein also refers to both TEM and STEM.

Several techniques are known for preparing TEM specimens. These techniques may involve cleaving, chemical polishing, mechanical polishing, or broad beam low energy ion milling, or combining one or more of the above. The disadvantage to these techniques is that they are not site-specific and often require that the starting material be sectioned into smaller and smaller pieces, thereby destroying much of the original sample.

Other techniques generally referred to as "lift-out" techniques use focused ion beams to cut the sample from a substrate or bulk sample without destroying or damaging surrounding parts of the substrate. Such techniques are useful in analyzing the results of processes used in the fabrication of integrated circuits, as well as materials general to the physical or biological sciences. These techniques can be used to analyze samples in any orientation (e.g., either in cross-section or in plan view). Some techniques extract a sample sufficiently thin for use directly in a TEM; other techniques extract a "chunk" or large sample that requires additional thinning before observation. In addition, these "lift-out" specimens may also be directly analyzed by other analytical tools, other than TEM. Techniques where the sample is extracted from the substrate within the FIB system vacuum chamber are commonly referred to as "in-situ" techniques; sample removal outside the vacuum chamber (as when the entire wafer is transferred to another tool for sample removal) are call "ex-situ" techniques.

Samples which are sufficiently thinned prior to extraction are often transferred to and mounted on a metallic grid covered with a thin electron transparent film for viewing. FIG. 1 shows a sample mounted onto a prior art TEM grid 10. A typical TEM grid 10 is made of copper, nickel, or gold.

Although dimensions can vary, a typical grid might have, for example, a diameter of 3.05 mm and have a middle portion 12 consisting of cells 14 of size 90×90 µm² and bars 13 with a width of 35 µm. The electrons in an impinging electron beam will be able to pass through the cells 14, but will be blocked by the bars 13. The middle portion 12 is surrounded by an edge portion 16. The width of the edge portion is 0.225 mm. The edge portion 16 has no cells, with the exception of the orientation mark 18. The thickness 15 of the thin electron transparent support film is uniform across the entire sample carrier, with a value of approximately 20 nm. TEM specimens to be analyzed are placed or mounted within cells 14.

For example, in one commonly used ex-situ sample preparation technique, a protective layer 22 of a material such as tungsten is deposited over the area of interest on a sample surface 21 as shown in FIG. 2 using electron beam or ion beam deposition. Next, as shown in FIGS. 3-4, a focused ion beam using a high beam current with a correspondingly large beam size is used to mill large amounts of material away from the front and back portion of the region of interest. The remaining material between the two milled rectangles 24 and 25 forming a thin vertical sample section 20 that includes an area of interest. The trench 25 milled on the back side of the region of interest is smaller than the front trench 24. The smaller back trench is primarily to save time, but the smaller trench also prevents the finished sample from falling over flat into larger milled trenches which may make it difficult to remove the specimen during the micromanipulation operation.

As shown in FIG. 5, once the specimen reaches the desired thickness, the stage is tilted and a U-shaped cut 26 is made at an angle partially along the perimeter of the sample section 20, leaving the sample hanging by tabs 28 at either side at the top of the sample. The small tabs 28 allow the least amount of material to be milled free after the sample is completely FIB polished, reducing the possibility of redeposition artifacts accumulating on the thin specimen. The sample section is then further thinned using progressively finer beam sizes. Finally, the tabs 28 are cut to completely free the thinned lamella 27. Once the final tabs of material are cut free lamella 27 may be observed to move or fall over slightly in the trench. A completed and separated lamella 27 is shown in FIG. 6.

The wafer containing the completed lamella 27 is then removed from the FIB and placed under an optical microscope equipped with a micromanipulator. A probe attached to the micromanipulator is positioned over the lamella and carefully lowered to contact it. Electrostatic forces will attract lamella 27 to the probe tip 29 as shown in FIG. 7. The tip 29 with attached lamella is then typically moved to a TEM grid 10 as shown in FIG. 8 and lowered until lamella is placed on the grid in one of the cells 14 between bars 13.

Whichever method is used, the preparation of sample for TEM analysis is difficult and time consuming. Many of the steps involved in TEM sample preparation and analysis must be performed using instruments operated manually. For this reason, successful TEM sample preparation generally requires the use of highly trained and experienced operators and technicians. Even then, it is very difficult to meet any reasonable standards of reproducibility and throughput.

Use of FIB methods in sample preparation has reduced the time required to prepare samples for TEM analysis down to only a few hours. However, CD metrology often requires multiple samples from different locations on a wafer to sufficiently characterize and qualify a specific process. In some circumstances, for example, it will be desirable to analyze from 15 to 50 TEM samples from a given wafer.

When so many samples must be extracted and measured, using known methods the total time to process the samples from one wafer can be days or even weeks. Even though the information that can be discovered by TEM analysis can be very valuable, the entire process of creating and measuring TEM samples has historically been so labor intensive and time consuming that it has not been practical to use this type of analysis for manufacturing process control.

What is needed is a method to more completely automate the process of TEM sample creation, extraction, and measurement and to increase throughput and reproducibility so that TEM measurement can be incorporated into integrated or in situ metrology for process control.

SUMMARY OF THE INVENTION

An object of the invention, therefore, is to provide an improved method for TEM sample analysis. Preferred embodiments of the present invention provide improved methods for TEM sample creation, extraction, measurement, and data handling, especially for small geometry (<100 nm thick) TEM lamella. Some preferred embodiments of the present invention provide methods to partially or fully automate TEM sample extraction and measurement, to make the process of creating and analyzing TEM samples less labor intensive, and to increase throughput and reproducibility of TEM analysis.

Another object of the invention is to reduce the time it takes to acquire data from TEM analysis of one or more sample sites so that TEM measurement can be incorporated into integrated or in situ metrology for process control. Preferred embodiments of the present invention also provide an in-line process for S/TEM based metrology on objects such as integrated circuits or other structures fabricated on semiconductor wafer. Computer aided design (CAD) data may be provided to enable the FIB system to locate the desired target structure at the sample sites. CAD data may also be provided to specify the locations for fiducial structures to be made with reference to the target structure.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Preferred embodiments of the present invention provide an in-line process for S/TEM based metrology on objects such as integrated circuits or other structures fabricated on semiconductor wafer. The process may be partially or fully automated and can be utilized in a wafer fabrication facility to provide rapid feedback to process engineers to troubleshoot or improve processes.

Other embodiments of the present invention provide improved methods for lamella creation, extraction, and measurement. A preferred embodiment can create S/TEM samples with a thickness in the 50-100 nm range for the purposes of S/TEM metrology with minimal site-to-site variation. The process can produce a 10 µm wide×~5 µm deep×~500 nm thick lamella with a final-thinned window of 3 µm×3 µm at the targeted final thickness (50-100 nm). The entire process is preferably fully automated and produces a lamella in roughly 18 minutes, with a site-to-site 3-sigma final lamella thickness variation of roughly 20 nm.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable.

Sample Management

Figure 1:
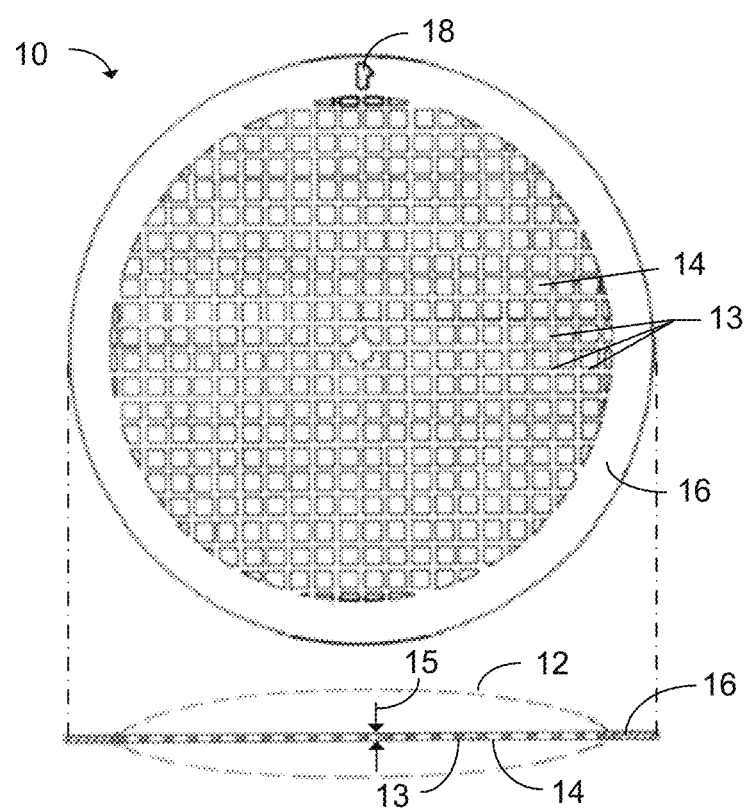
FIG. 1 shows a typical prior art TEM grid.
Figure 2:
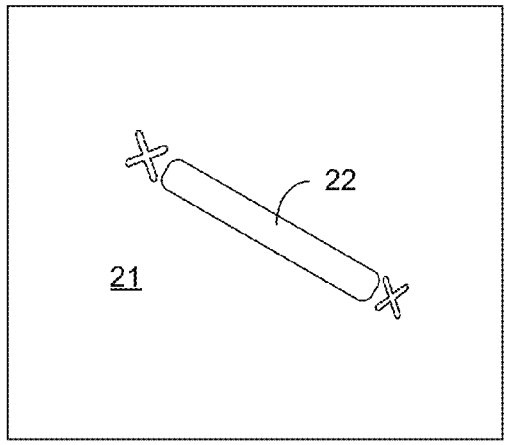
FIGS. 2-5 illustrate the steps in an ex-situ sample preparation technique according to the prior art.
Figure 3:
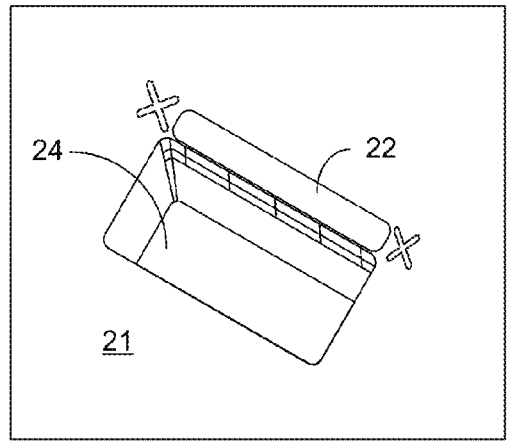
Figure 4:
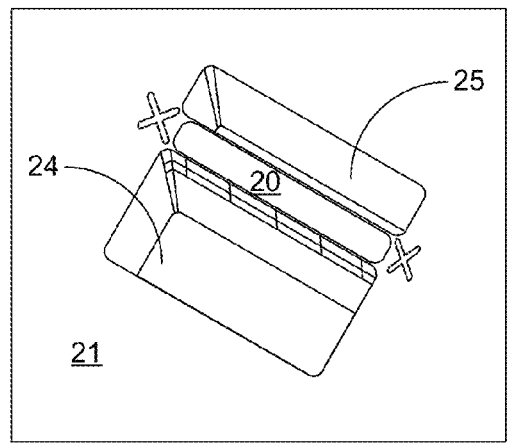
Figure 5:
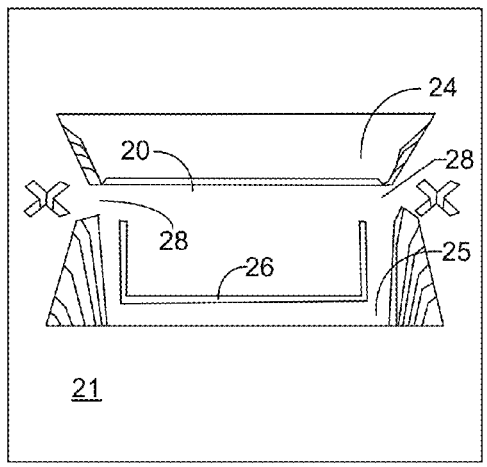
Figure 6:
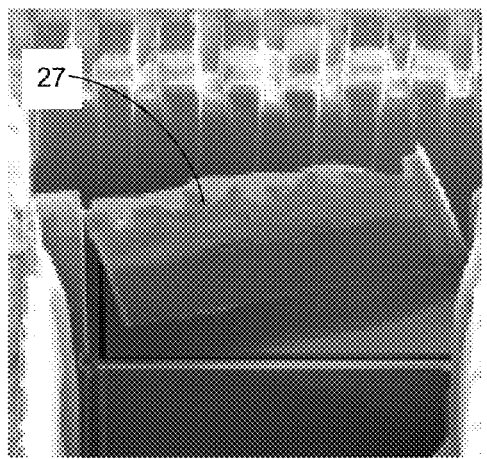
FIG. 6 is a micrograph of a completed and separated lamella according to the prior art.
Figure 7:
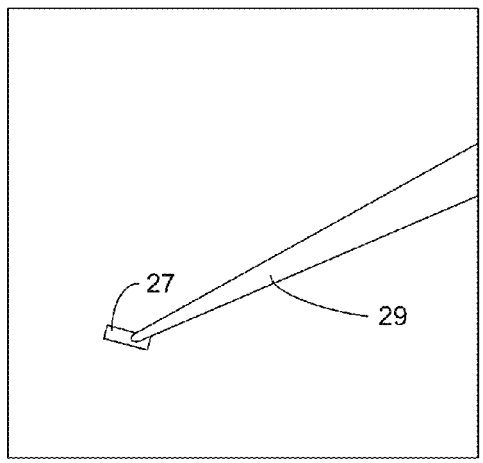
FIGS. 7-8 illustrate the transfer of a lamella using a probe and electrostatic attraction according to the prior art.
Figure 8:
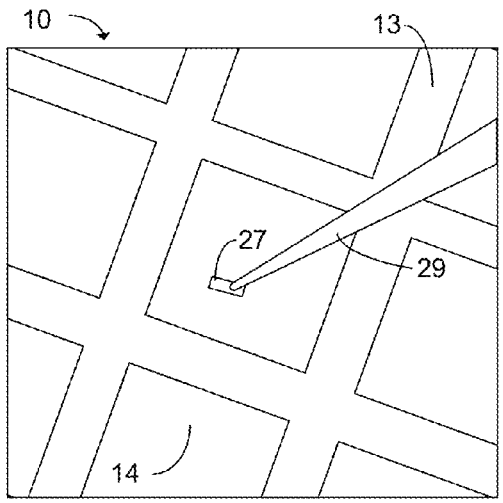
Figure 9:
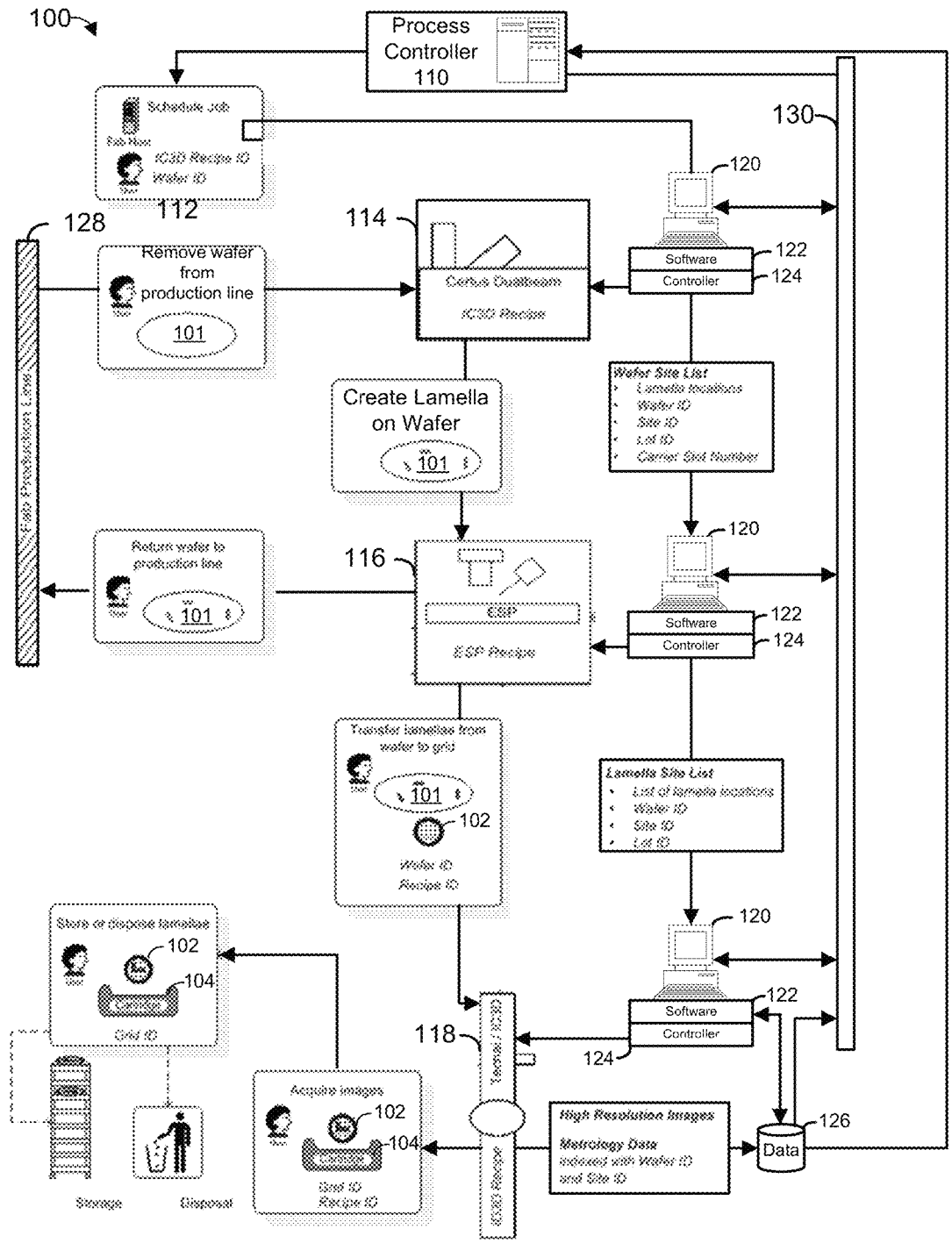
FIG. 9 illustrates automated S/TEM sample management according to the present invention.

FIG. 9 illustrates automated S/TEM sample management according to the present invention. In the preferred embodiment of FIG. 9, TEM samples are processed by a cluster of different processing tools having the capability of sequentially processing samples (e.g., lamellae extracted from semiconductor wafers). The S/TEM sample management tool suite 100 generally includes a Process Controller 110 and a Fab Host computer 112 operably connected to (or integrated with) a FIB system 114, a lamella extraction tool 116, and a S/TEM system 118. In a preferred embodiment, FIB system 114 comprises a dual beam FIB/SEM system such as the Certus/CLM available from FEI Company of Hillsboro, Oreg., the assignee of the present invention; and S/TEM system 118 comprises a system such as a Tecnai G2 S/TEM also available from FEI Company. In the preferred embodiment of FIG. 9, each processing tool is operably connected to (or integrated with) a computer station 120, which uses software 122 for implementing TEM sample creation and processing. Any suitable software (conventional and/or self-generated) applications, modules, and components may be used for implementing software. For example, in the embodiment of FIG. 9, the automated S/TEM sample management is implemented using IC3D™ software for automated machine control and metrology, which is also available from FEI Company.

With reference to FIG. 9, in one embodiment, Process Controller 110 is shown connected to computer stations 120 through network 130. Network 130 may be any suitable network configuration, such as a virtual private network ("VPN"), local area network ("LAN"), wide area network ("WAN") or any combination thereof. Similarly, computers for performing process controller 110 functions, Fab Host 112 functions, controller 124 function, computer station 120 functions, or data storage 126 functions may be any suitable computing devices such as desktop computers, laptop computers, PDAs, server systems, mainframes, processing systems made from discrete components, and/or combinations of one or more of the same. They can execute conventional operating systems such as Windows™, Unix™ Linux™, Solaris™ and/or customized, job-specific operating systems. The depicted devices can be implemented with any suitable combination of conventional (albeit possibly modified) equipment, and in many system embodiments, may not even be included. (For example, the network 130 may not be utilized.)

Figure 10:
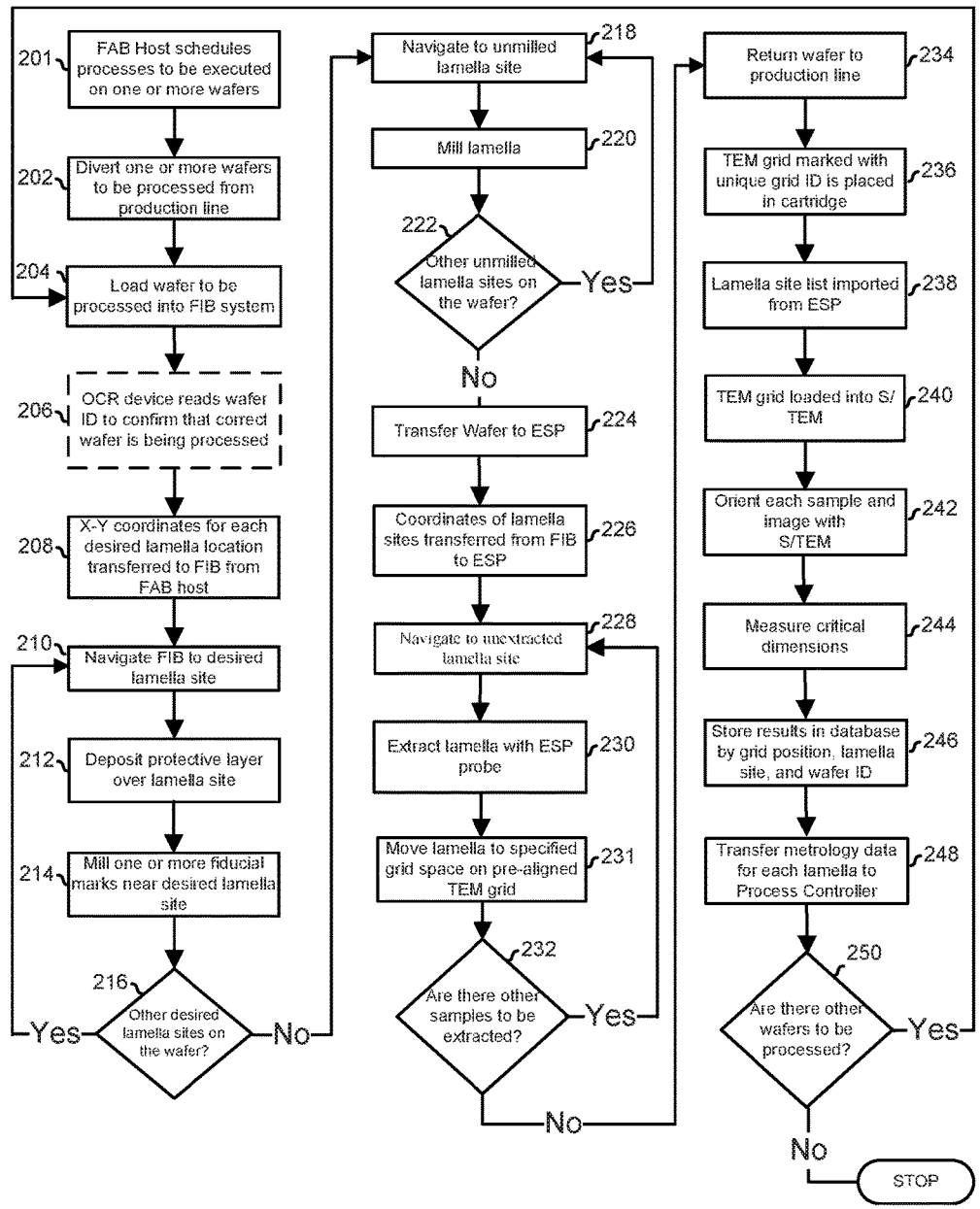
FIG. 10 is a flowchart showing the steps of creating, processing, and measuring one or more TEM samples according to a preferred embodiment of the present invention.

FIG. 10 is a flowchart showing the steps of creating, processing, and measuring one or more TEM samples according to a preferred embodiment of the present invention. In step 201, at the front end of the CD-S/TEM metrology process, Fab Host 112 schedules one or more specified processes to be executed on a particular wafer. The processes can be input by an operator or selected from a menu of available recipes. Alternatively, processes or recipes can be scheduled by Process Controller 110. Each processing tool is coupled to a controller 124, which receives instructions from the Fab Host as well as wafer identification information. Each controller 124 also interacts with software 122, such as the IC3D™ software for automated machine control and metrology.

Wafers 101 are preferably uniquely identified by a wafer ID number or other designation. Optionally, the wafer ID information can be etched into the surface of the wafer. The specified processes can include, for example, instructions or recipes for locating desired lamella sites, imaging lamella sites using the SEM or FIB, milling fiducial marks at specified locations based upon image processing and metrology, milling lamellae at precise locations on the wafer surface, and analyzing lamella samples using S/TEM analysis. In most cases, all the specified processes are preferably performed automatically, with little or no user intervention. The metrology process can be controlled by matching a particular recipe to be run with the particular wafer ID.

In step 202, one or more wafers 101 are then diverted from the production line 128. Wafers are preferably transferred by way of a multi-wafer carrier and auto-loading robot, as in well known in the art, although wafers can also be transferred manually. After a carrier has been transferred to the FIB system, in step 204, the wafer residing in a specified slot of the carrier is loaded into FIB system 114, such as a Certus Dual Beam System, to mill TEM lamellae at desired locations. Optionally, in step 206, an OCR device can read the ID etched into the wafer surface to confirm that the correct wafer will be processed.

Once wafer 101 is loaded into the FIB device 114, in step 208, the site for each desired lamella is located. The FIB device can use x-y coordinates provided by the FAB host 112 to roughly locate lamella sites. In step 210, the FIB navigates to a desired lamella site. Optionally, in step 212, a protective layer is deposited over the site. Then in step 214, one or more fiducial marks are milled nearby. Alternatively, one or more of the fiducials could be located on the lamella to be removed. Also, in some embodiments, the fiducial marks could be created by known techniques other than ion beam milling, for example by SEM or FIB deposition or by SEM milling. Preferably, high-precision fiducial marks are employed and the exact locations for each fiducial mark and each lamella can be determined by pattern recognition based upon automated machine-vision based metrology and image recognition, as discussed in greater detail below and in co-pending PCT App. No. PCT/US07/82159, filed on Oct. 22, 2007, which is hereby incorporated by reference. If there are other lamella sites on the wafer, in step 216, the process returns to step 210 and repeats steps 210 to 216 at each desired lamella site.

Once all lamella sites have been located and the desired fiducials milled, in step 218, the FIB navigates to an unmilled lamella site. In step 220, a lamella is created at each desired location using the process described below with reference to FIG. 11. After all desired lamellae have been milled, the samples are extracted from the wafer 101 and loaded onto a TEM grid 102. Lamellae extraction can be conducted according to a number of known methods, either in-situ or ex-situ. In a preferred embodiment, once the lamellae have been milled, in step 224, the entire wafer is transferred to a separate lamella extraction tool 116 such as an Ex-Situ Plucker ("ESP"), discussed below. Wafers are preferably transferred by way of a multi-wafer carrier and auto-loading robot, as in well known in the art, although wafers can also be transferred manually. In step 226, a wafer site list (including, for example, Site IDs, list of the x-y coordinates for each lamella location, Wafer ID, Lot ID, and Carrier Slot Number) is retrieved from the FIB system 114 by the lamella extraction tool 116. Alternatively, the wafer site list could be provided by the FAB Host or other process controller. Skilled persons will appreciate that whenever information or instructions are passed from one device to another as discussed herein, the transfer can be implemented using a number of well-known methods, including direct transfer (tool to tool) or through other devices or controllers (such as through a process controller).

In step 228, ESP 116 uses a mechanical stage to navigate to the site of an unextracted lamella. In step 230, the lamella is extracted, for example, using a mechanical/electrostatic/pressure manipulator and placed onto a TEM grid in step 231. A new TEM grid will preferably be used to mount lamellae from all sites at specified locations on the grid so that TEM data can be properly mapped to the appropriate wafer location. If there is another lamella to be extracted, in step 232, the process returns to step 228 and repeats steps 228 to 232 for each unextracted lamella.

Once all the lamellae have been extracted and the TEM grid 102 populated, in step 234, the wafer 101 and grid 102 are unloaded from the lamellae extraction tool 116, and wafer 101 is then returned to the production line. Again, wafers are preferably transferred by way of a multi-wafer carrier and auto-loading robot, as in well known in the art, although wafers can also be transferred manually. In step 236, the populated grid 102 is placed in a cartridge 104 uniquely marked by the grid identification number. In step 238, a lamella site list is imported from the lamella extraction tool. The lamella site list preferably contains, among other data, the grid coordinates for each placed lamella, the corresponding Site IDs, the Wafer ID, and the Lot ID.

In step 240, the populated grid 102 is then loaded into a TEM/STEM system. In step 242, the samples are imaged by the S/TEM. Prior to S/TEM imaging, automatic orientation routines can be used to ensure that each lamella is properly oriented for imaging. A preferred auto-orientation routine can use pattern recognition powered via IC3D along with automated stage moves and beam-shifts to rotate and center each lamellae relative to the electron beam. Other routines can be used to raise or lower the stage so that each sample is imaged at the proper operational height within the tool. A predefined region of interest on the lamella can be used to give the framework for the automatic orientation routines. Once that region of interest is defined it can be imaged and the image evaluated, for example via material contrast or sharpness, to determine the best fit for all axes of the sample orientation to ensure that it is normal to the electron beam (Alpha and Beta orientation).

In step 244, the critical dimensions measured, and in step 246, the results are stored in a local IC3D database. After imaging, the grid can be discarded or placed into storage. The metrology data for each lamella can be exported from the database to the process controller 110 in step 248 and used for both upstream and downstream process control. If there are other wafers to be processed in step 250, the process returns to step 204 and the next wafer is loaded. The entire process repeats until all wafers have been processed.

Lamella Creation

Current TEM lamella creation processes for FIB systems use manual input as the primary method for locating a feature or site of interest for lamella creation. Typically, once the desired lamella location is manually located, a fiducial or locating mark is milled nearby. Because FIB imaging necessarily causes some sample damage, a protective layer is deposited over the desired lamella location before imaging and/or milling. The protective layer makes it harder to see features on the substrate so a fiducial mark is typically milled into the protective layer to help orient the beam and locate the proper place for a cut. This fiducial is used in subsequent processing as a locating mark. Image recognition keyed to this fiducial is then used to find the locations for subsequent milling of the lamella. In order to mill the fiducial, a location near the desired lamella site is typically selected manually, and the desired fiducial pattern is then automatically milled at that location.

This method of manually identifying the lamella site and then manually selecting the fiducial location does not provide a high degree of precision or accuracy. As a result, known automatic lamella milling routines are limited to rough milling of lamellae which are approximately 500 nm thick. Further thinning is typically manually controlled in order to achieve the desired lamella thicknesses of 100 nm or less.

Figure 11:
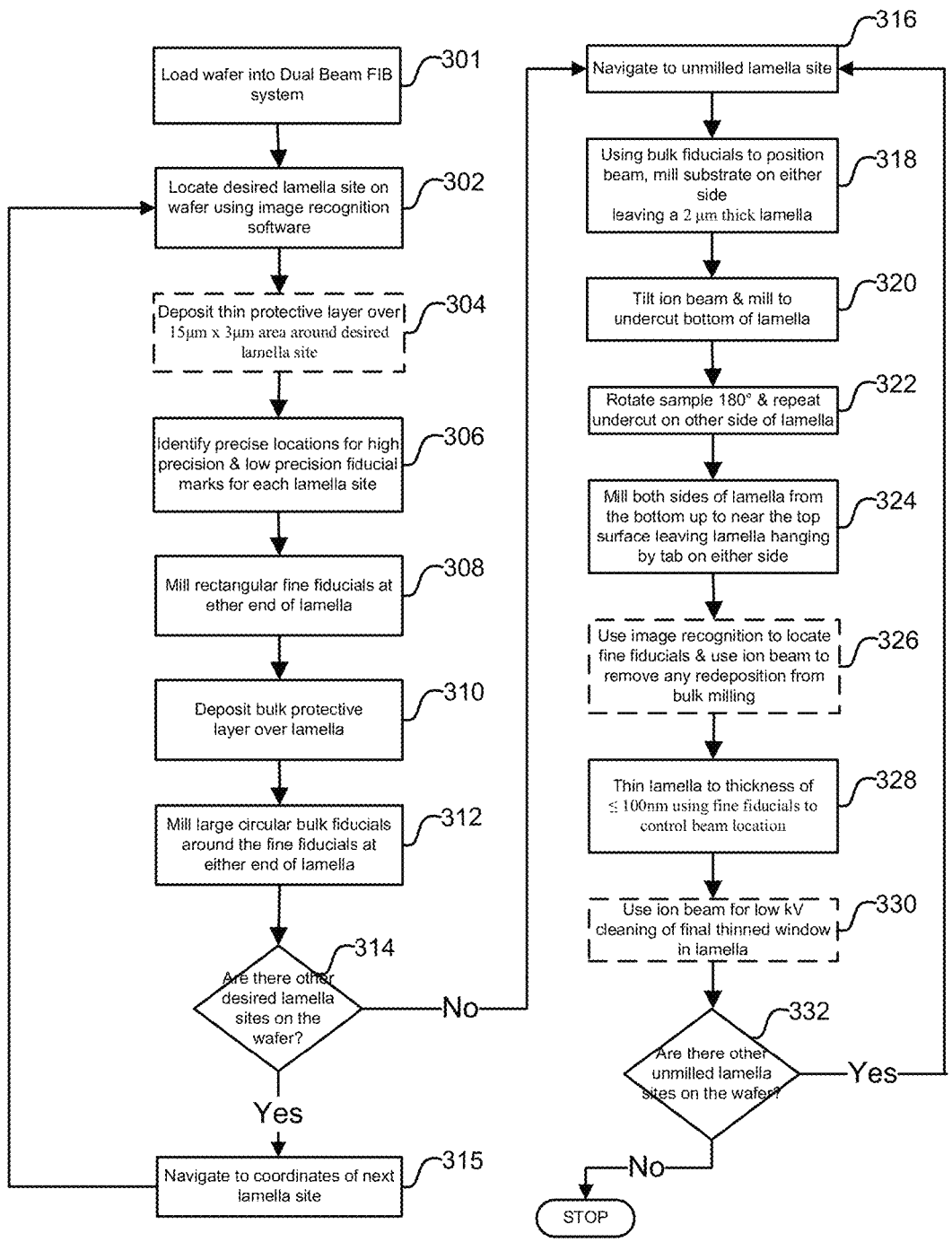
FIG. 11 is a flowchart showing the steps of creating one or more lamellae according to a preferred embodiment of the present invention.

FIG. 11 is a flowchart showing the steps of creating one or more lamellae according to a preferred embodiment of the present invention. In this embodiment, machine-vision based metrology and image recognition, high-precision fiducial marks, and automatic fiducial placement are used to significantly improve lamella placement accuracy and precision. Various steps in the process are shown in FIGS. 5 through 11.

First, in step 301, a wafer is loaded into a FIB system, such as a Certus Dual Beam System, commercially available from FEI Company of Hillsboro, Oreg., the assignee of the present invention. In step 302, lamella sites on the wafer surface are located automatically using image recognition software. Suitable image recognition software is available, for example, from Cognex Corporation of Natick, Mass. Image recognition software can be "trained" to locate the desired lamella locations by using sample images of similar features or by using geometric information from CAD data. Automated FIB or SEM metrology can also be used to identify or help identify the lamella site. Metrology may consist of image-based pattern recognition, edge finding, ADR, center-of-mass calculations, blobs, etc.

In optional step 304, the lamella site is given a protective 5 kV FIB tungsten deposition 15 µm wide by 3 µm tall for 1:20. This provides sufficient tungsten on the site surface to prevent damage during the 30 kV FIB site alignment and deposition steps. This protective layer may be directly placed if the 5 kV180 pA FIB aperture to SEM coincidence is less than 4 µm, otherwise a process of site alignment may be used to refine placement of this deposition.

In step 306, the precise locations of any desired fiducial marks with respect to each desired lamella location are specified. For example, using a FIB or SEM to image a sample location, a fiducial location could be specified by an operator using a mouse to drag a virtual box around the desired fiducial location. Automated metrology software could then precisely measure the location of the fiducial with respect to identifiable features at the sample location (for example 15 nm from the right edge of the feature). When each lamella site is located, a fiducial can then be automatically milled at each lamella site at the precise location specified so that the spatial relationship between each fiducial and each lamella location will be identical. A fiducial location could also be specified using CAD data to specify the location of the fiducial with respect to a particular structure on the wafer surface.

In a preferred embodiment, precise fiducial placement is accomplished through the use of the IC3D™ software's vision tools. A specified pattern can be located by image recognition software and used to locate a target structure. A series of calipers—a pattern recognition tool that locates edges—are then used to find the edges of the target structure and to precisely center the fine fiducials around the target structure. Extensive use of IC3D's shape linking capabilities allows robust placement of site fiducials based on direct measurement of each site.

Preferably, a combination of high precision (fine) fiducials and low precision (bulk) fiducials are used to optimize lamella placement precision and accuracy. Currently, fiducials used for lamella location and milling consist only of low-precision features such as an "X" formed by the intersection of two milled lines. At the resolutions necessary for adequate lamella production, however, each milled line will be several nanometers wide. Edge detection software must be used to determine the centerline of each milled line and then the intersection of the two mathematically determined centerlines used to determine a particular reference point. There is typically too much error in this type of determination to use the fiducial to accurately determine a lamella location within the margin of error needed for many small-geometry lamella applications.

Figure 12:
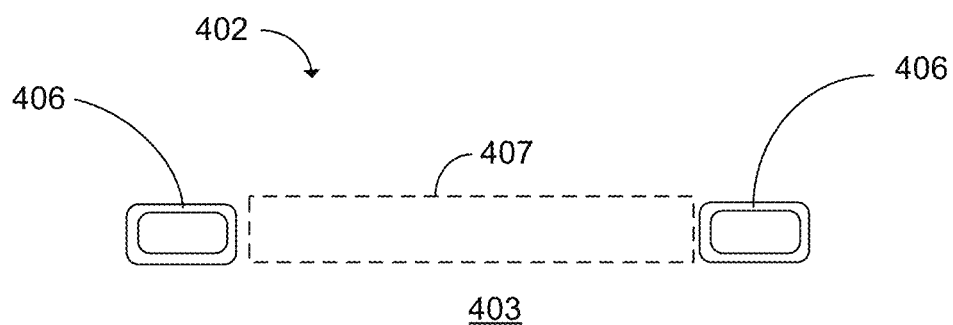
FIG. 12 shows a lamella site according to the process of FIG. 11 after high precision fiducials have been milled and a protective layer deposited over the lamella location.

In a preferred embodiment, a combination of typical low-precision fiducial marks and higher precision marks are used. High-precision fiducials, such as the rectangles 406 shown in FIG. 12 allow the lamella location to be much more accurately determined. The rectangular fiducials 406 shown in FIG. 12 are located at either end of the desired lamella location 427. High-precision fiducial are smaller than the low-precision fiducials discussed below. For this reason, the high-precision fiducials are not identifiable with the large FIB beams used for bulk milling, and are only used for final placement of the lamella with smaller FIB beams. The rectangular fiducials in FIG. 12 are located using image analysis to determine the Y position of their top and bottom edges. This results accurate positioning even when the fiducial is damaged during FIB imaging. Edge detection software only has to identify the top and bottom edges to precisely locate the top and bottom edges of the lamella. Pattern recognition for these rectangular fiducials is based on a two-measurement strategy—the top and bottom edges of the fiducial are measured. Once the edge positions are located, a central line or axis can be determined which is parallel to the top and bottom edges of the lamella. As the substrate 403 is imaged with the FIB, the top surface is progressively sputtered away. The high precision fiducial described above is very tolerant of this FIB damage because both measured edges will be altered at nearly the same rate, so the overall error in lamella placement will be very low.

Figure 13:
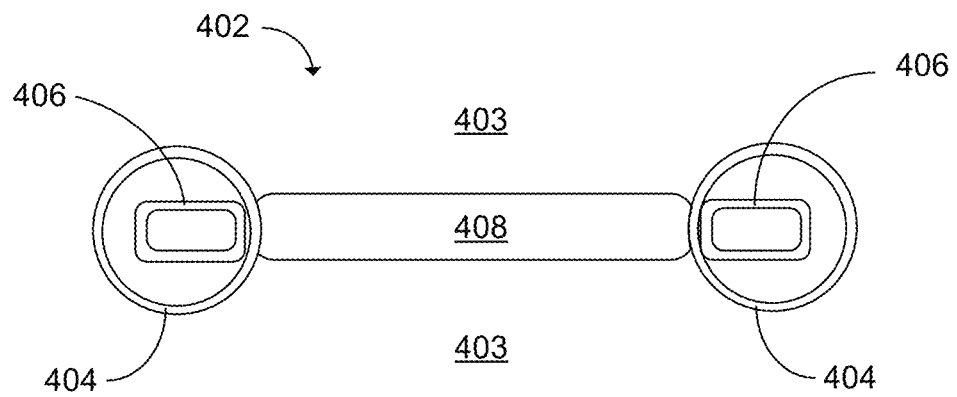
FIG. 13 shows a lamella site according to the process of FIG. 11 after low precision fiducials have been milled.

Low-precision fiducials, such as the large circles 404 in FIG. 13, can be used for gross-structure pattern recognition, such as quickly finding the approximate lamella location and performing the bulk milling. Suitable low-precision fiducials can be easily identified when the sample is imaged with a low resolution (higher beam size) ion beam suitable for rapid bulk material removal. Multiple fiducials and combinations of low and high precision fiducials and different fiducial shapes (as shown in FIG. 13) can be used for even more accurate orientation.

Once the fiducial locations have been determined, in step 308, high precision fiducials are milled at the desired locations. As shown in FIG. 12, a small rectangular feature 406 is milled at each end of the lamella site (which is indicated by dashed line 407) with the 1 nA 30 kV FIB for vertical placement of the lamella during the final thinning process. In a preferred embodiment, a suitable fiducial pattern will allow the final lamella placement to be accurate within 10 nm. In some embodiments, the size and shape of the fiducial can be varied depending on the size, width, or location of the desired lamella.

In step 310, after the high precision fiducials have been milled, a bulk protective layer 408 composed of, for example, tungsten or platinum is deposited over the lamella site to protect the sample from damage during the milling process. FIG. 13 shows a lamella site 402 with a protective layer 408 deposited over the desired lamella location on a wafer surface 403. For some samples where information is required very close to the surface, it may be useful to deposit the protective layer using a low energy FIB (~5 keV) to perform the deposition. The high precision fiducials 406 are also preferably lightly backfilled with the protective material to protect them during future processing.

In step 312, after the bulk protective deposition, large circular fiducials 404 as shown in FIG. 13 are milled around the fine fiducials. These low-precision fiducials are used for gross-structure pattern recognition, such as quickly re-finding the approximate lamella location and determining the location for bulk milling of the lamella. Because a larger beam size will be used for the bulk milling, a suitable low precision fiducial should be easily identified by pattern recognition software even in lower resolution images. The system can then readily relocate each desired lamella site by locating the fiducial and knowing that the lamella site is positioned at a fixed offset from the fiducial.

Figure 14:
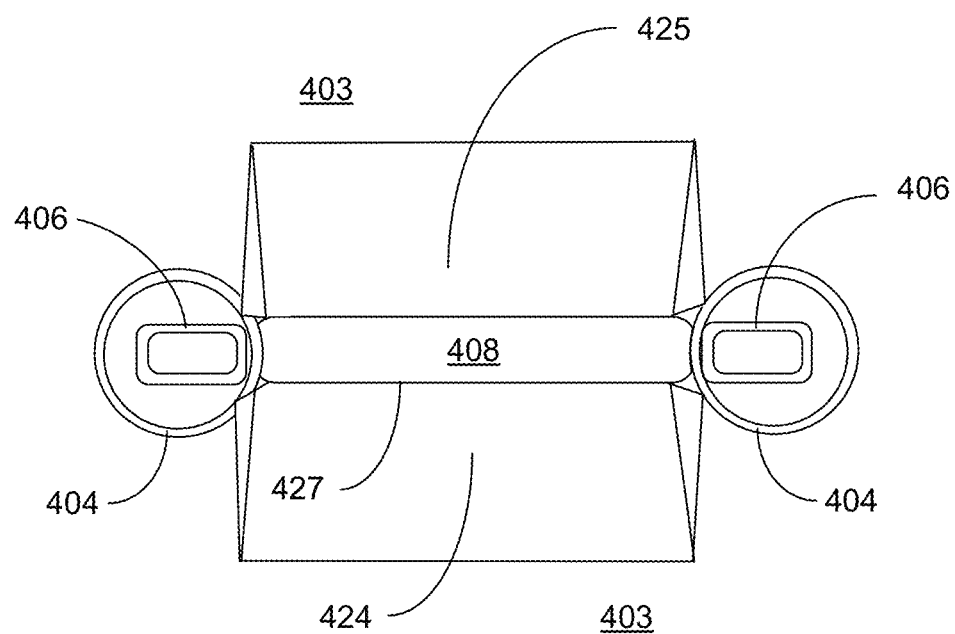
FIG. 14 shows a lamella site according to the process of FIG. 11 after bulk milling has been completed.

If there are other lamella sites on the wafer in step 314, the FIB system navigates to the coordinates of the next lamella site (step 315). The process then returns to step 302 and steps 302 to 314 are repeated for all remaining lamella sites before the lamella milling process is started. Once fiducials have been milled at all lamella sites, in step 316, the FIB system navigates to an unmilled lamella site. In step 318, bulk substrate milling is used to roughly shape the lamella. FIG. 14 shows a lamella site after the bulk milling of step 318 has been completed. A larger ion beam size will be suitable for bulk material removal. In a preferred embodiment, each lamella will be formed by using a FIB to cut two adjacent rectangles 424, 425 on a substrate, the remaining material between the two rectangles forming a thin vertical sample section 427 that includes an area of interest. Preferably, an ion beam will be directed at the substrate at a substantially normal angle with respect to the substrate surface. The beam will be scanned in a rectangular area adjacent to the sample section to be extracted, thus forming a rectangular hole 424 having a predetermined depth. The milled hole should be sufficiently deep to include the feature of interest in the extracted sample. Preferably, the milled hole is also deep enough to allow for bulk material to remain at the bottom of the thinned sample (beneath the feature of interest) to increase the mechanical rigidity of the sample as discussed below. The beam will be scanned in a rectangular area 425 adjacent to the sample section to be extracted, but on the opposite side of said sample section from the first rectangular hole. The remaining material between the two rectangular holes will preferably form a thin vertical sample section that includes the lamella to be extracted.

Figure 15:
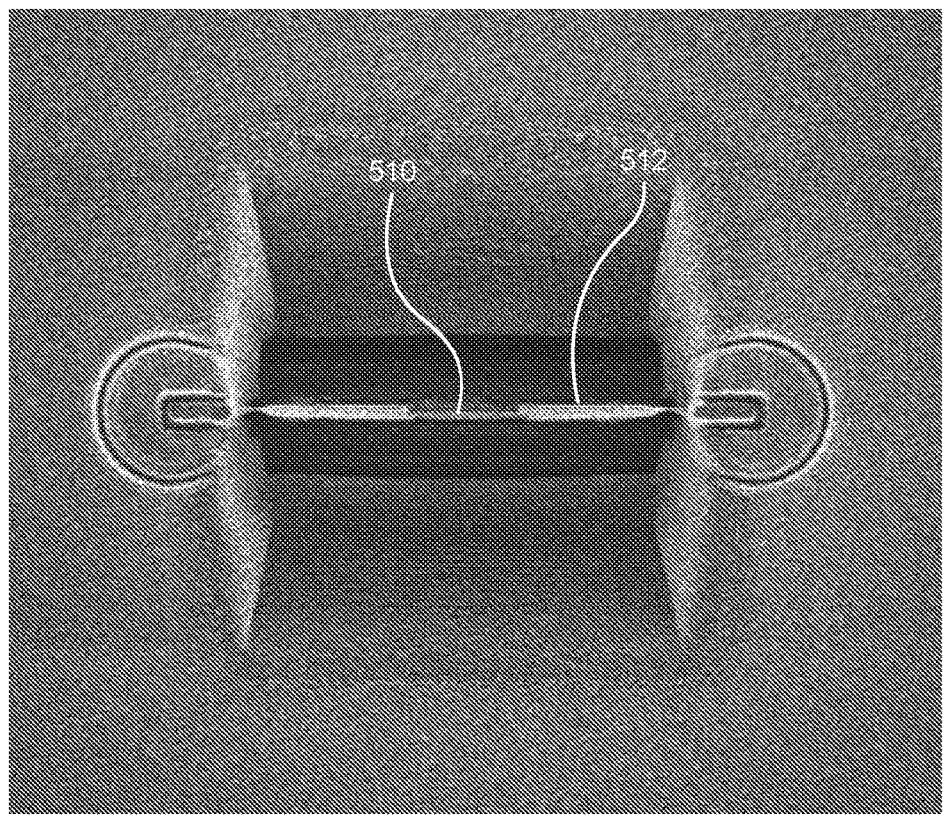
FIG. 15 shows a high resolution micrograph of a lamella sample according to the present invention after bulk milling has been completed.

Low-precision fiducials 404 can be used to control the beam location for bulk milling of the lamella (using a larger beam diameter for more rapid sample removal). A typical cross-section mill pattern can be used coming in from both sides of the lamella, leaving a coarse lamella approximately 2 μm thick. The lamella is then further thinned to approximately 800 nm with a cleaning cross-section mill on both sides in preparation for the undercut step. FIG. 15 shows a high resolution micrograph of a lamella sample after bulk milling has been completed.

Figure 16:
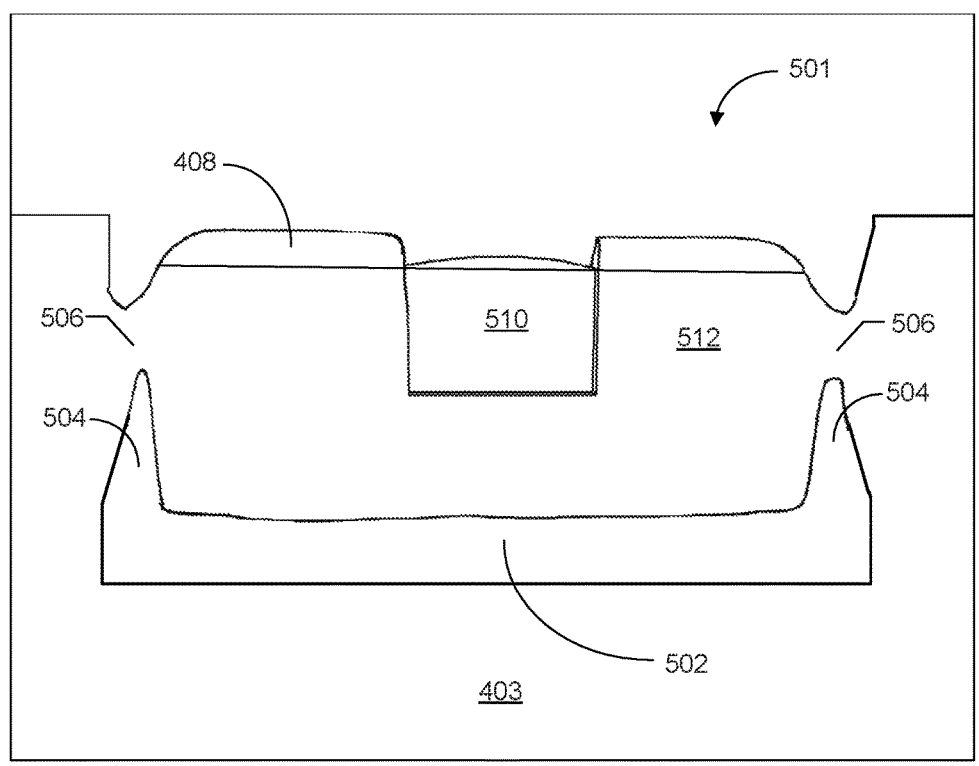
FIG. 16 shows a lamella created according to the process of FIG. 11.

In step 320, after the fiducials and bulk mills are done, the lamella undergoes an undercutting process. The FIB column is preferably tilted to approximately 4.5 degrees and the lamella bottom undercut with a cleaning cross-section at 1 nA. Alternatively, the sample stage could be tilted. The precise location for the undercut can be located using vision tools to locate and measure the fine fiducials. Although a greater FIB tilt could be employed (subject to hardware constraints) a shallow incidence angle undercutting provides two benefits to the TEM sample preparation process. First, the lamella face is not imaged at a high incidence angle, thus reducing Ga+ implantation and damage; and second, the undercutting process serves as an intermediate thinning step that has been shown to reduce the lamella thickness to a reasonably narrow range of widths for a number of different substrates (TI SiGe, TI STI, MetroCal, IFX DTMO, Fujitsu contact). The undercut 502 and side cuts 504 for a lamella sample 527 are shown in FIG. 16.

In step 322, the sample is then rotated 180 degrees and the process repeated on the top edge of the lamella in order to cut the bottom free. This results in a rough lamella that is roughly 500 nm thick centered around the target structure.

In step 324, two cuts are made from the bottom of the lamella up to near the top surface in order to cut the sides of the lamella free, but leaving the lamella hanging by a tab 506 (shown in FIG. 16) on either side at the top of lamella. Once the final thinning of the lamella has been completed, a probe can be attached to the lamella and the tabs or hinges severed so that the lamella can be extracted. Alternatively, a probe can be used to break the lamella hinges as described below and in co-pending PCT App. No. PCT/US07/82030, filed on Oct. 20, 2007, which is hereby incorporated by reference.

In optional step 326, IC3D vision tools can be used to locate the fine fiducials and remove any redeposition from the bulk milling process as well as the protective tungsten layer deposited during the fiducial milling process.

The lamella formed by the first two rectangular bulk-milling cuts and the undercutting will preferably be roughly 500 nm thick. In step 328, the center portion 510 of the lamella (containing the area of interest) is thinned from both sides, preferably using a 30 pA beam at 1.2 degrees of FIB tilt with the mill pattern described below. As discussed below, the typical cleaning mill pattern commonly used for lamella milling causes very thin lamellae (<100 nm) to bend or bow. Applicants have discovered that using a mill pattern resulting in multiple passes of the beam on the sample face prevents the sample from bowing. This mill pattern, along with other embodiments of a method for eliminating lamella bowing during the thinning process, is discussed in greater detail below.

The final thinning cuts can be placed using calipers (with image recognition) to find the lamella edges, with the final lamella thickness being determined by an offset in the milling position from the lamella face. For example, for each lamella to be extracted from a sample, the exact location of the lamella can be determined from the fiducial location. The first cut is milled at half the desired lamella thickness away from the center of the desired sample. Viewing the sample from the top down, using either FIB or SEM imaging, automated metrology software can then measure the edge of the first cut and the fiducial location and precisely determine the location of the second cut. Using the location of the high precision fiducials to precisely control beam location, the lamella can then be thinned using a finely focused FIB to a thickness of 100 nm or less in a process that is also highly repeatable.

Preferably, real time pattern recognition can be used to position the FIB. A suitable FIB system providing real time pattern recognition and metrology is the Certus 3D Dual Beam System available from FEI Company, the assignee of the present invention.

In optional step 330, low-kV cleaning is performed on the final thinned window with a 180 pA 5 kV FIB at 4.5 degrees of tilt. Applicants have discovered that a 10 second cleaning mill on each face of the lamella produces a significant improvement in TEM imaging conditions.

If there are other unmilled lamella sites on the wafer, in step 332, the FIB system navigates to the coordinates of the next unmilled lamella site. The process then returns to step 316 and steps 316 to 332 are repeated for all remaining unmilled lamella sites.

Figure 17:
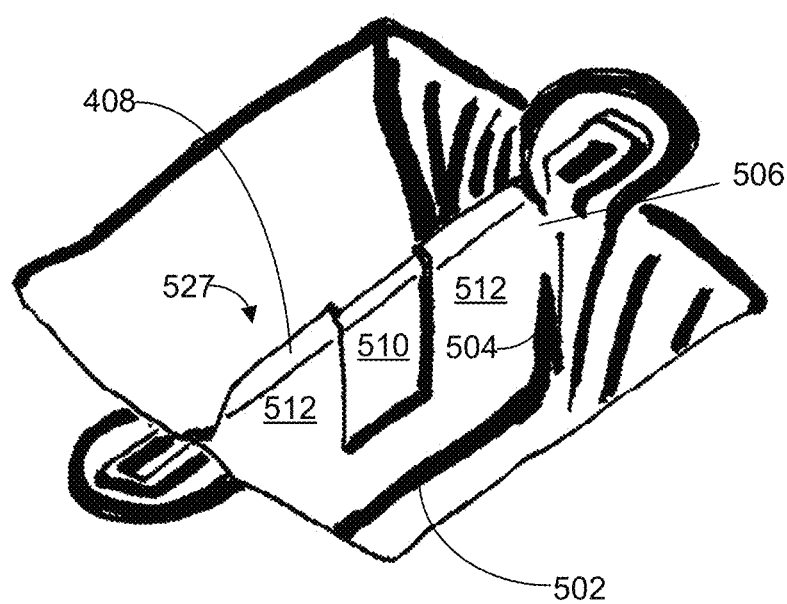
FIG. 17 shows a lamella created according to the process of FIG. 11.
Figure 18:
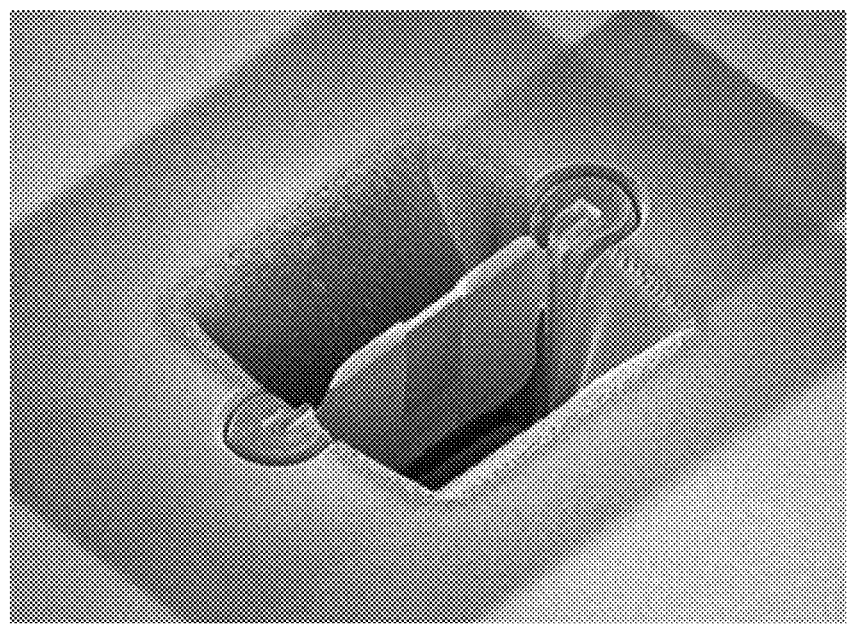
FIG. 18 shows a high resolution micrograph of a lamella according to the present invention.

The final lamella structure produced by the method of discussed in reference to FIG. 11 is shown in FIGS. 16-18. As discussed below, a center lamella "window" 510 can be thinned to a thickness of 100 nm or less, leaving thicker surrounding material to provide the sample with increased mechanical strength. Preferably, the center window is approximately 3 μm wide, 4 μm deep, and 50-70 nm thick. The thicker material surrounding window 510, indicated by reference numeral 512 in FIG. 15, also helps prevent the lamella from bowing during the milling process. The increased mechanical strength of this "windowed" lamella structure is also very desirable when using an ex-situ lamella extraction device as described in co-pending PCT App. No. PCT/US07/82030, filed on Oct. 20, 2007, which is incorporated by reference. FIG. 18 shows a high resolution micrograph of a lamella created using the process described above.

Figure 19A:
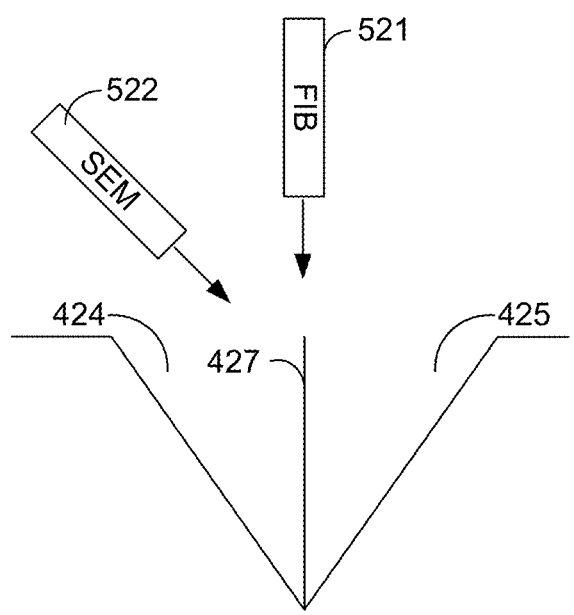
FIG. 19A shows a graphical representation of a dual beam system where one beam is used to thin the lamella while the other beam images the lamella to endpoint milling.
Figure 19B:
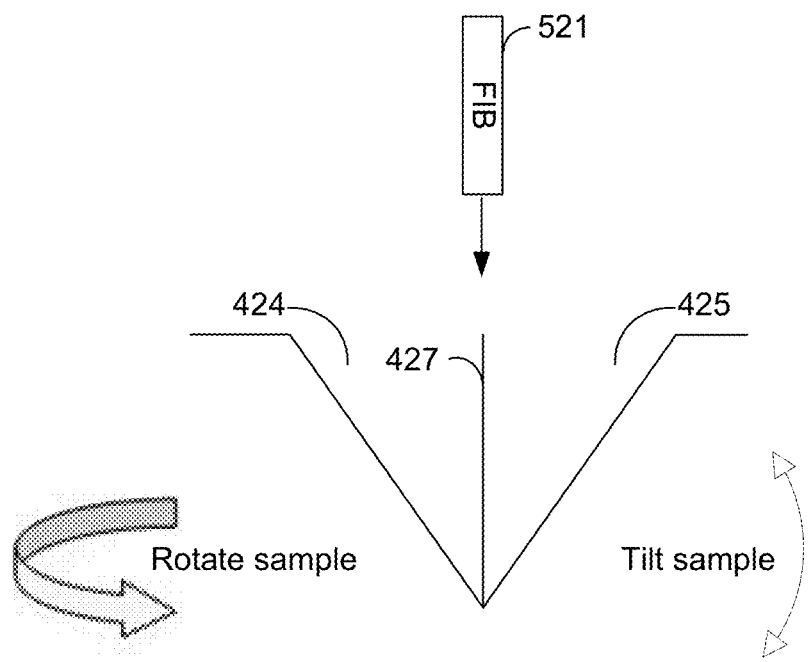
FIG. 19B shows a graphical representation of a single beam system where the sample must be rotated to allow one beam to mill and image for endpointing.

In addition to determining mill locations relative to fiducial marks as discussed above, the milling process can be endpointed using top down pattern recognition and metrology. In a preferred embodiment, FIB milling is carried out in a dual beam FIB/SEM system, as shown schematically in FIG. 19A (not to scale) with vertically mounted FIB column 521 used to mill substrate 403 to create lamella 427 and the SEM column 522 used to image the lamella 427 so that automated metrology software can determine whether the lamella 427 has been thinned to the desired thickness. Alternatively, a dual FIB system could be used with one beam used to mill and the other used to image. As shown schematically in FIG. 19B (not to scale), a system with a single FIB column 521 could also be used and the sample tilted and rotated so that the same beam could be used to mill and image (as is known in the prior art). Skilled persons will recognize that there is a danger of damage to the lamella if a FIB is used to image the sample.

Figure 19C:
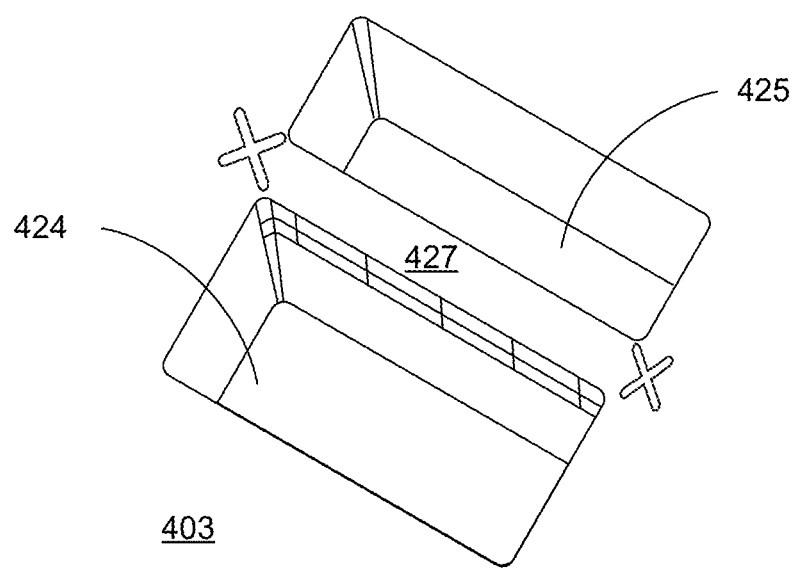
FIG. 19C shows a lamella site during the milling process which could be imaged and the image processed according to the present invention to endpoint milling.

Referring also to FIG. 19C, after the initial bulk mill 424 is completed on one side of the lamella 427, the endpoint of the second bulk mill 425 can be controlled by monitoring the width of the lamella in the same fashion that cross-sections for sub-100 nm features are measured by a CD-SEM.

Typically, to measure the width of cross-section of a structure, a SEM is used in conjunction with automatic metrology software. As the electron beam is scanned across the exposed cross-section, whether secondary or backscattered detection is employed, there will typically be a change in electron intensity at the edges of the structure. An algorithm is used to assign an edge position based upon the contrast at the edges of the structure and to determine the distance between those edges.

A preferred embodiment of the present invention makes a novel application of these known techniques for cross-section metrology. The final lamella position and thickness would be based on a mill and image technique similar to known slice and view techniques where the FIB in a dual beam system is used to expose a sample cross section and the SEM is used to image the sample for automated metrology analysis. Image processing tools such as pattern recognition and edge finding tools can thus be used to precisely control lamella thickness. These types of prior art "slice and view" techniques are described, for example, in U.S. patent application Ser. No. 11/252,115 by Chitturi et al. for "Method Of Measuring Three-Dimensional Surface Roughness Of A Structure," which is hereby incorporated by reference, and which is assigned to FEI Company, the assignee of the present invention.

Preferably, thinning would first be completed on one side of the lamella. The location of the initial milling would be controlled using fiducial location or other metrology as discussed above. The sample would then be imaged from the top down with either a focused ion beam or scanning electron microscope. As with a CD-SEM, when either the ion beam or the electron beam strikes the surface of substrate, secondary electrons and backscattered electrons are emitted. Respectively, these electrons will be detected by a secondary electron detector or backscattered electron detector as is known in the art. The analog signal produced either by secondary electron detector or backscattered electron detector is converted into a digital brightness values. As the beam (either ion or electron) is scanned across the lamella surface, there will be a change in emitted electron intensity at the edges of the structure. An algorithm is used to assign an edge position based upon the difference in brightness values or contrast at either of the edges of the structure and to determine the distance between those edges. If analysis of the image determines that certain specified criteria are not met (such as, for example, a minimum desired lamella/sample width) then the mill and image processing steps are repeated.

Lamella Extraction and Mounting

In a preferred embodiment of the present invention, once a number of lamellae have been created on a wafer, as discussed above, the lamellae can be automatically extracted from the wafer surface and placed onto a TEM grid for S/TEM analysis. Preferably, the lamella extraction and mounting is carried out ex-situ by transferring the entire wafer from the FIB system to a separate lamella extraction tool such as an Ex-Situ Plucker ("ESP"), described herein. Wafers are preferably transferred to the ESP by way of a multi-wafer carrier and auto-loading robot, as in well known in the art, although wafers can also be transferred manually. The list of all lamella sites for each wafer ID is retrieved from the FIB system 114 by the ESP. Lamella extraction tool 116 uses a mechanical stage to navigate to each lamella site. The lamellae are extracted using a vacuum/electrostatic manipulator and placed onto a TEM grid. The lamella extraction process is preferably fully automated. Alternatively, the extraction process can be completely or partially controlled manually.

Figure 21:
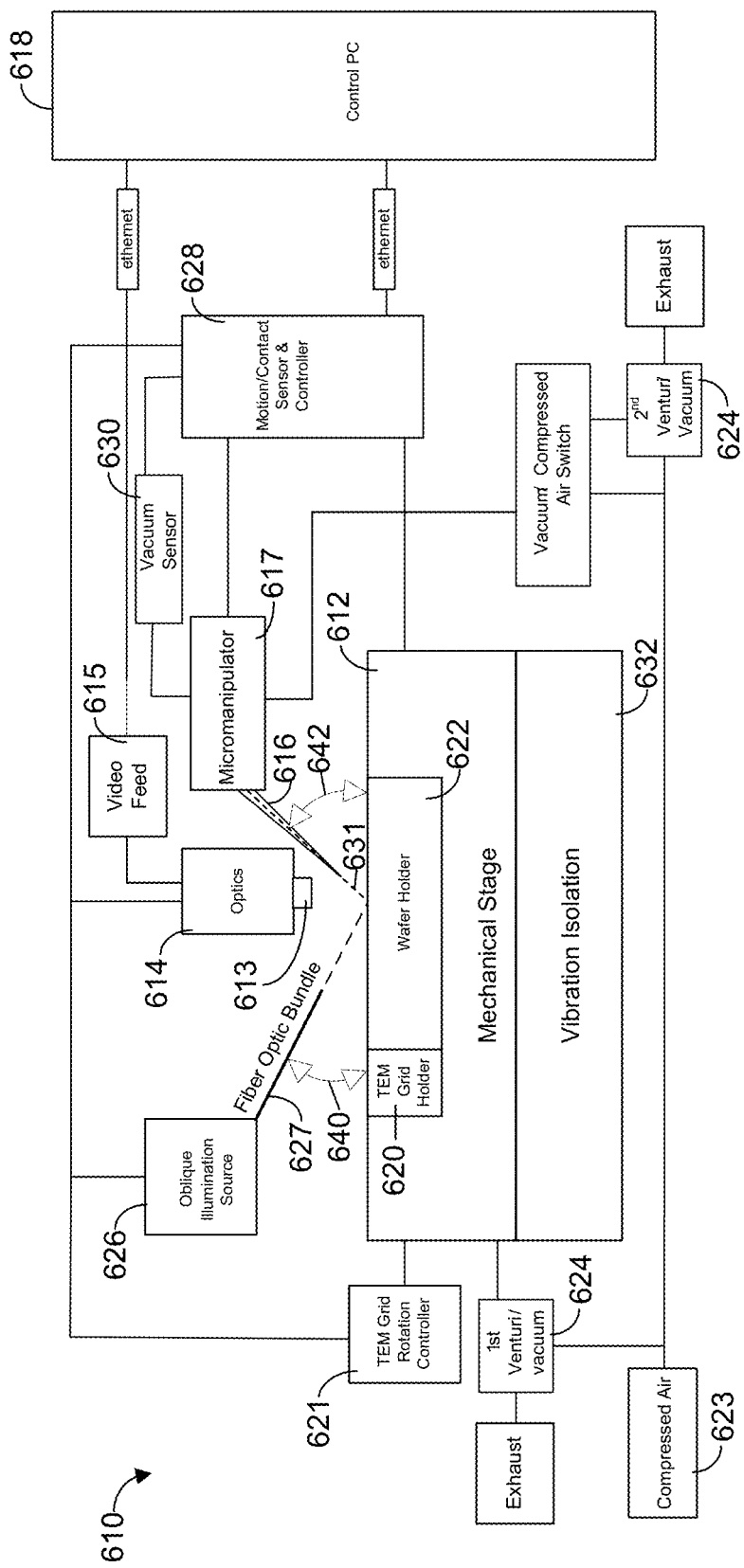
FIG. 21 shows an ex-situ lamella extraction device according to the present invention.
Figure 25:
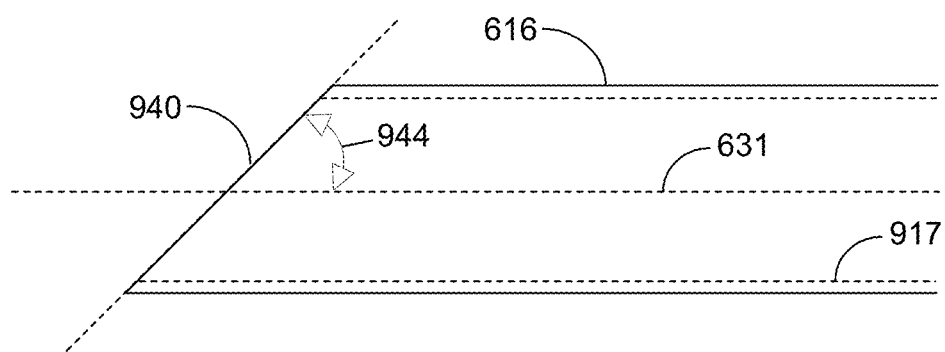
FIG. 25 shows a beveled probe according to the present invention.

FIG. 21 is a block diagram showing a preferred embodiment of ex-situ sample extraction tool 610 (hereinafter "Ex-Situ Plucker" or "ESP") according to the present invention. In a preferred embodiment, the ESP is a standalone tool for ex-situ extraction of samples. The ESP comprises a TEM specimen extractor having a mechanical stage 612, an optical microscope 614 with a video feed 615, and a probe 616 (also referred to herein as a microprobe) for extracting the samples. Referring also to FIG. 25, probe 616 preferably comprises a cylindrical hollow tube with a flat tip beveled at approximately 45 degrees through which a vacuum can be applied in order to draw the sample to the probe tip. Probe 616 is oriented so that the cylindrical (longitudinal) axis of the probe is at an approximately 45 degree angle relative to the wafer (substrate) upper surface. Where the sample to be extracted has a vertical sample face, this results in the probe being also oriented at a 45 degree angle relative to the sample face. Probe 616 preferably comprises a pulled 1 mm borosilicate tube with a face beveled at 45 degrees. Suitable probes can be manufactured, for example, by using standard borosilicate micropipettes with the tips modified by using a micropipette puller such as a Narishige PC-10 to create long, thin micro-capillaries with an outer diameter of 10 to 12 μm.

In one preferred embodiment, the ESP comprises the following components that are integrated and controlled via a single control point (e.g. a Control PC) 618: a wafer holder 622 mounted on an XYZR mechanical substrate stage 612, a micromanipulator system 617 including a probe holder and motors and an XYZ probe stage that can rotate a microprobe about cylindrical (longitudinal) axis of a probe, a rotatable TEM grid holder 620, a TEM grid rotation controller 621, an optional separate grid stage (not shown) (both the wafer holder and the TEM grid holder can be mounted on one mechanical stage), a pulled micromachined micropipette probe 616 with 45 degree flat tip (possibly roughened to minimize adhesion), an optional controlled environment to minimize effects of humidity and temperature (not shown), one or more vacuum pumps 624 or other devices for applying vacuum through the probe 616, an air pressure source 623 such as a source of compressed air, an optical microscope 614 with lens 613 to image the substrate, a light optical system 626 (using a fiber optic bundle 627) used to illuminate the substrate from an oblique angle 640 to facilitate imaging and/or machine-based pattern recognition, a motion/contact sensor and controller 628, an air flow or vacuum sensor 630, and a vibration isolation table 632.

In the preferred embodiment of FIG. 21, the ESP is operably connected to (or integrated with) a computer station 618, which uses software for implementing sample extraction and manipulation. Computer station 618, through appropriate software, can receive the x-y coordinates for the sample to be extracted from the FIB system used to create the lamella. The location of each lamella can then be matched with a corresponding TEM grid location once the samples are extracted and transferred to the TEM grid (typically one lamella per cell). This allows for data traceability through the entire process so that the final TEM results can be automatically matched back to the particular sample site on the original wafer. Computer station 618 is also preferably operably connected to the stage controllers and micromanipulator controllers to position the sample and grid stages and to position the microprobe.

By applying a small vacuum pressure to the lamella through the microprobe tip, the lamella can be controlled much more accurately than by using electrostatic force alone as in the prior art. The lamella is held securely in place and is not as easily dropped as in the prior art. Minimizing the electrostatic attraction between the probe tip and the sample (as discussed in greater detail below) makes it much more likely that the sample will stay precisely where it is placed rather than continuing to adhere to the probe tip. Even where electrostatic attraction is used to adhere the sample to the probe tip (in whole or in conjunction with vacuum pressure) the angled bevel on the microprobe, along with the ability to rotate the probe tip 180 degrees around its long axis, allows the lamella to be placed down flat on the TEM grid film, which tends to maximize the attraction between the sample and the TEM grid film causing the sample to adhere to the film and stay at the position where it is placed. This allows sample placement and orientation to be precisely controlled, thus greatly increasing predictability of analysis and throughput (because the TEM stage does not need to be adjusted as often between samples).

Figure 22:
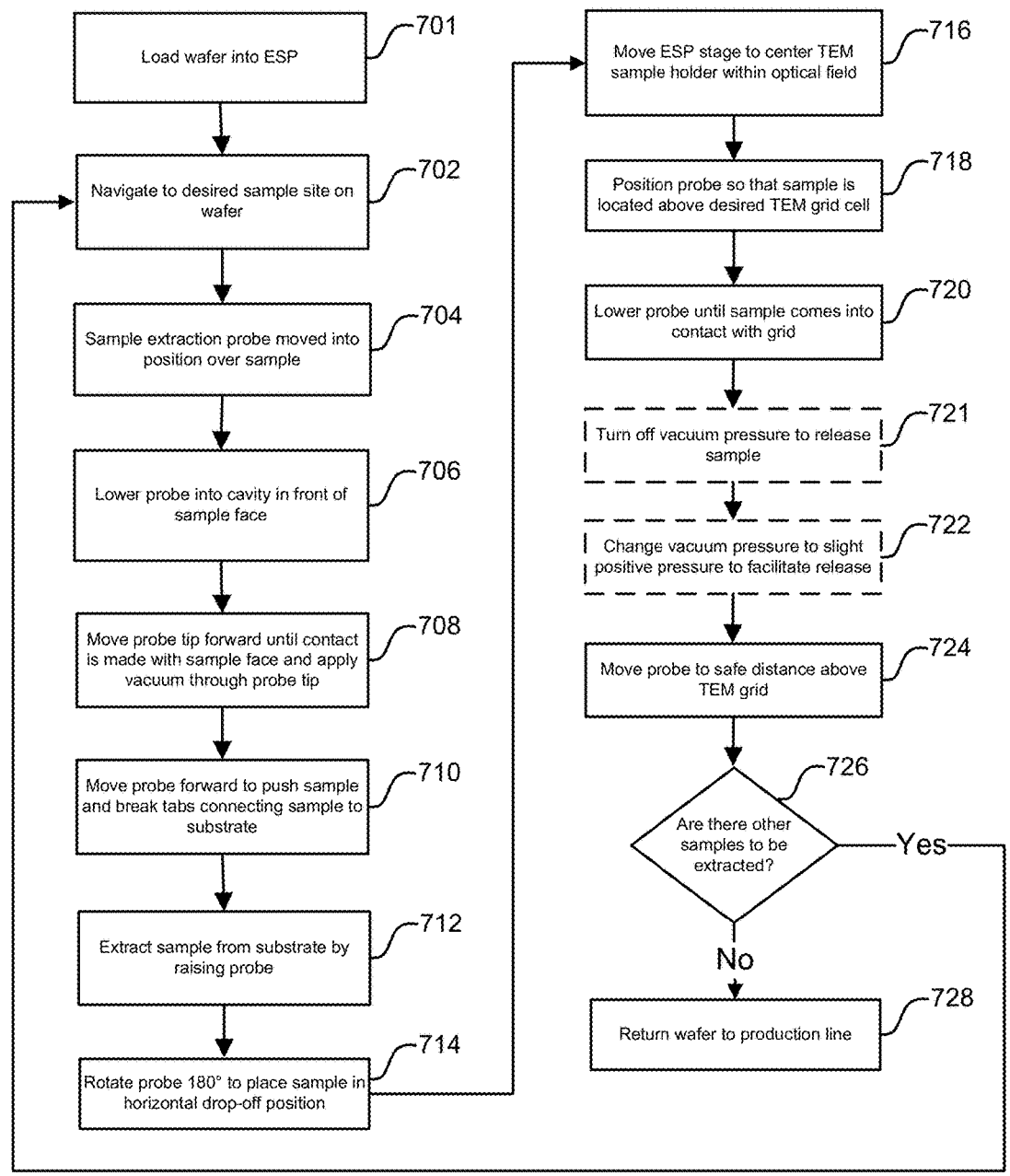
FIG. 22 is a flowchart showing the steps in extracting a sample using an ex-situ sample extraction device according to the present invention.

FIG. 22 is a flowchart showing the steps in extracting multiple samples from a wafer according to the present invention. These steps are preferably carried out and controlled automatically by computer station 618 via computer readable instructions, although the steps can also be completely or partially controlled manually.

In step 701, a wafer containing milled but unextracted samples is loaded into the ESP wafer holder 622. In a preferred embodiment, the samples have been created as discussed above in reference to FIGS. 2 to 6, except that the lamellae are preferably only partially separated from the substrate leaving a small tab of material at either end holding the lamella in place. The wafer holder 622 is mounted on an XYZR mechanical substrate stage. The wafer can be aligned automatically or manually using known methods.

Figure 26A:
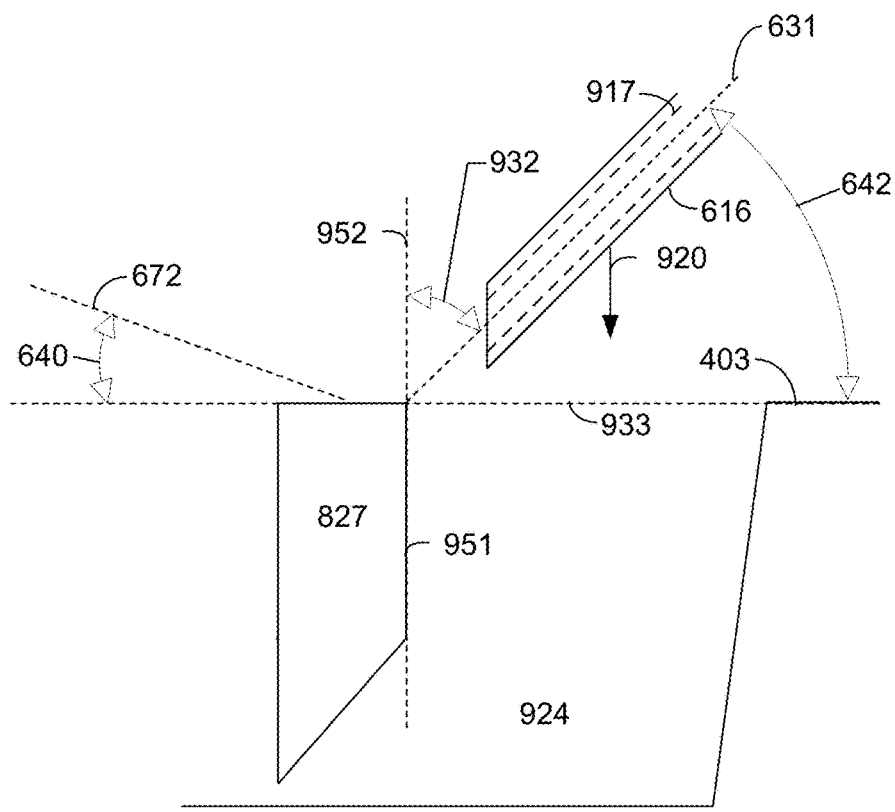
FIGS. 26A-26B illustrate lowering a probe tip into contact with a sample to be extracted according to the present invention.
Figure 26B:
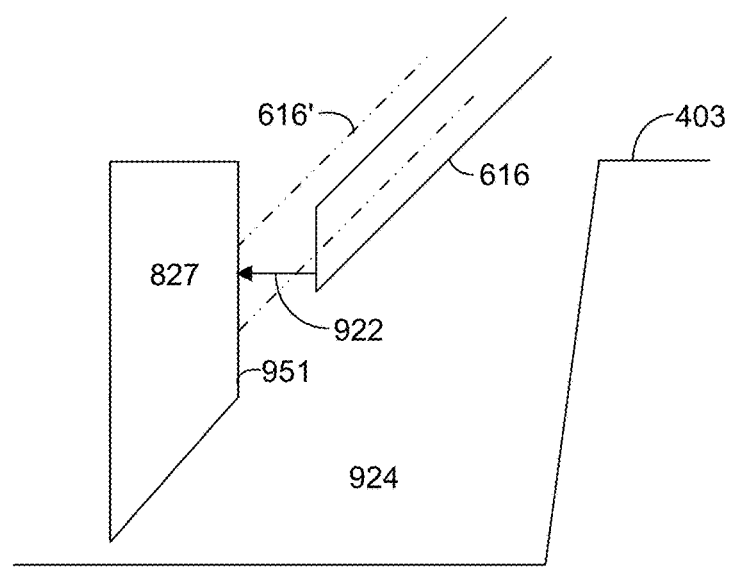
Figure 27:
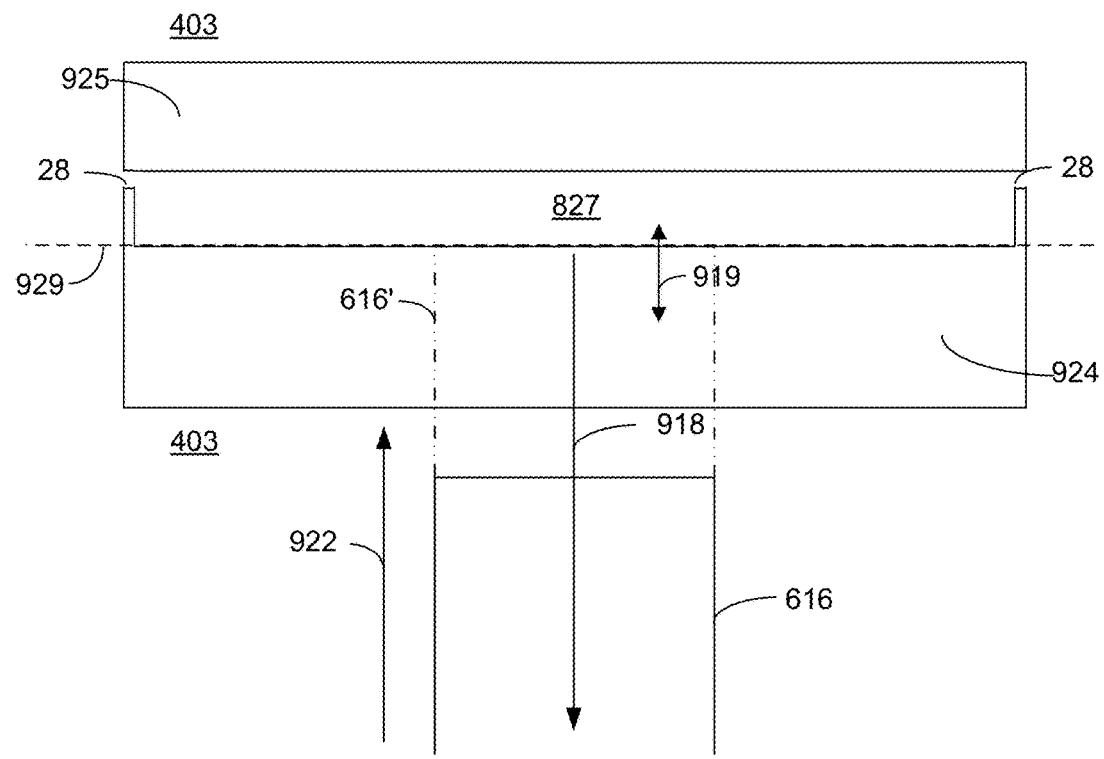
FIGS. 27-28 illustrate moving a probe tip into contact with a sample to be extracted according to the present invention.
Figure 28:
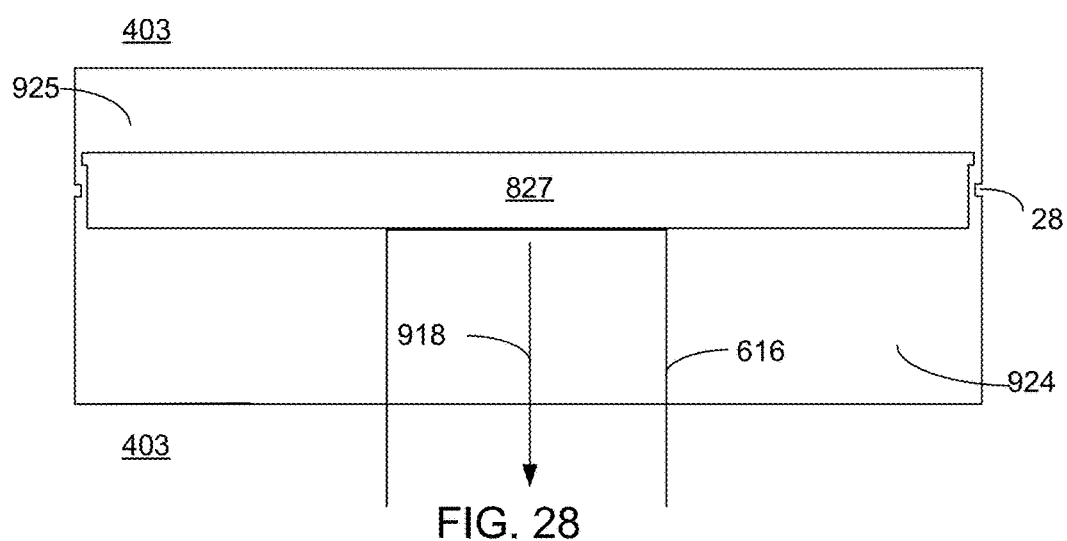

After the wafer substrate is aligned, in step 702, the ESP can navigate to a sample site using positional data imported from the FIB system used to create the samples. The ESP optical microscope 614 is used to image the substrate at the sample site. The exact sample location and orientation is determined and the probe is moved into position. Referring also to FIGS. 27-28, the sample stage is rotated so that the orientation of the probe is generally perpendicular to the lamella face (although as shown in FIGS. 21 and 26A-B the probe will typically be tilted down so that the intersection of the cylindrical axis of the probe 631 with the plane of the substrate surface forms an acute angle 642). In other words, the cylindrical axis of the probe lies in a plane which is perpendicular to the sample face. This process can be performed by an operator viewing the sample site by using manual controls to move the probe and/or the substrate to position the probe tip in the milled cavity behind the sample. In a preferred embodiment, this process can be performed automatically using machine-based image recognition.

Both oblique and bright field illumination should be used to facilitate sample location and grid alignment. The oblique illumination should be used to image the lamella cavity to locate the lamella to be extracted. Referring also to FIGS. 21, 26A, and 27, assuming that the lamella itself lies in the X-Y plane 929, the illumination 672 will preferably be directed in a plane perpendicular to the X-Y plane of the lamella 827 and at an acute angle 640 relative to the substrate surface so that light reflecting off of the surface of the substrate 403 will not enter the acceptance angle of the lens 613 of the optical microscope 614. More preferably, the illumination will be directed at an angle of approximately 20 degrees relative to the substrate surface.

Figure 23:
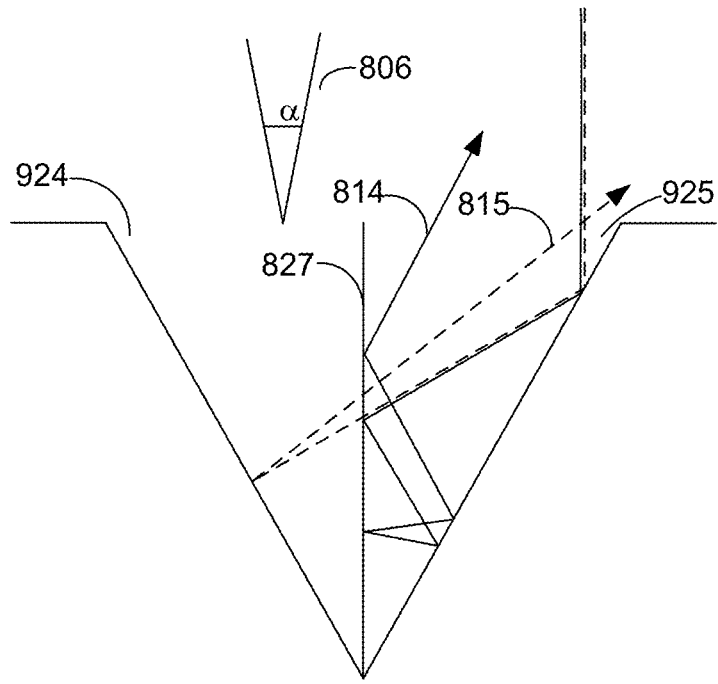
FIG. 23 is an example of a ray diagram showing the possible path of a beam of light when using top down illumination.
Figure 24:
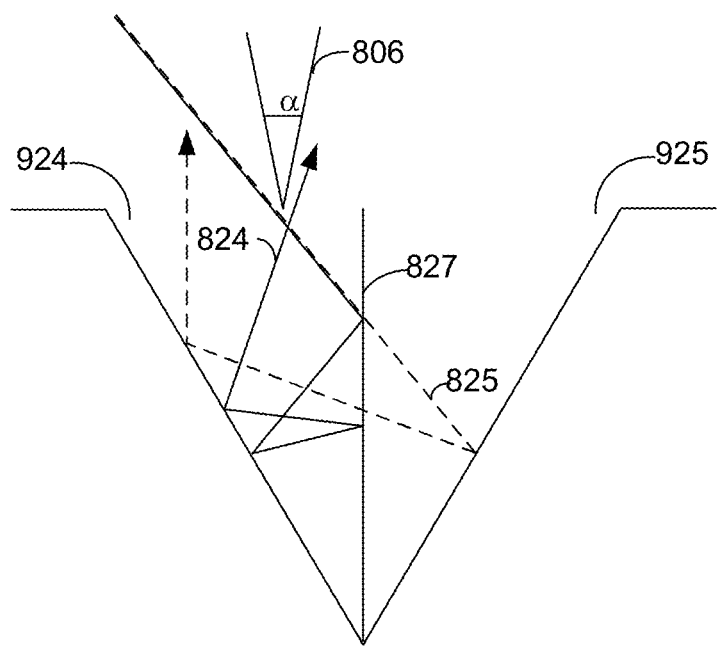
FIG. 24 is an example of a ray diagram showing the possible path of a beam of light when using oblique illumination.

Due to the angled walls of the lamella cavity, very poor image contrast is achieved within the cavity with top down illumination, since very little light enters the acceptance angle of the lens. As shown in FIGS. 23 and 24, due to the multiple reflections that will occur within the cavity, the amount of signal will be highly dependent on the wall angles within the cavity, these may vary significantly from one application to another. As a result, in some circumstances the illumination may need to be directed at an angle other than the 90 degree angle described above. In a preferred embodiment, the illumination angle should be adjustable, either manually by an operator or automatically. Bright field illumination can be used to allow imaging of alignment marks and TEM grids.

Unfortunately, sometimes a lamella may be missing from a cavity or positioned improperly. It that event, it is important to be able to quickly determine whether the lamella is present. In FIG. 23, dashed line 815 represents top-down illumination with no lamella present. As shown in FIG. 23, with top down illumination into the lamella cavity 924, 925 and no lamella present, the light rays 815 will undergo multiple reflections and will not reenter the acceptance angle 806 of the lens (not shown). Likewise, with lamella 827 present in the cavity 924, 925, light rays (shown by solid line 814) will also reflect at an angle outside acceptance angle 806. Thus, with top down illumination, the entire lamella cavity 924, 925 will appear dark (whether or not a lamella 827 is present).

With oblique illumination, however, more reflected light enters the lens. As shown in FIG. 24, dashed line 825 represents oblique illumination with no lamella present. In that case, light rays will reflect off the two cavity sidewalls and enter the lens. Thus, the left half of the cavity 924 will appear brighter when the lamella is absent. Line 824 represents oblique illumination with the lamella 827 in place. In that case, reflected light will tend to escape the lens and the cavity 924, 925 will appear dark (although the top of the lamella 827 may be visible.) Thus, with oblique illumination it can be readily determined whether a lamella is still within the cavity and whether it is at approximately the expected position. Depending upon the slope of the cavity walls and of the lamella face, the proper illumination angle may be adjusted with respect to the wafer plane and with respect to an axis perpendicular to the wafer to optimize sample location.

The oblique illumination can be supplied, for example, by way of a fiber optic bundle mounted at an appropriate oblique angle relative to the substrate surface. Preferably, the illumination source will be mounted opposite the probe and nanomanipulator so that the sample to be extracted can be positioned with the illumination coming from one side and the probe from the other. It is also preferable that the illumination source be mounted in the same plane as the probe. As a result, rotating the sample stage so that the lamella face is perpendicular to the probe will also position the sample properly relative to the illumination source.

In step 704, the sample extraction probe is moved into position over the sample to be extracted. As shown in FIGS. 25-28, in order to extract the sample, the ESP probe tip 940 is oriented so that it is roughly perpendicular to the desired probe attachment site, typically in the center of the sample as shown in FIGS. 27-28. As shown in FIGS. 25-26, the ESP probe tip 940 is also preferably beveled at an angle 944 of approximately 45 degrees, and the entire ESP probe 616 is oriented at an angle 642 of approximately 45 degree relative to the wafer upper surface (shown by dashed line 933). Where the sample to be extracted has a vertical sample face, this results in the angle 932 of probe 616 relative to the sample face (shown by dashed line 952) also being a 45 degree angle. As a result, the beveled probe face is substantially parallel to the sample face. The internal walls of the probe are indicated by dashed lines 917.

To extract the sample, in step 706, the ESP probe is lowered into the cavity in front of the sample face, such as the rectangular area 924 adjacent to one of the sample faces 951 as shown in FIGS. 26A-26B. The arrow 920 in FIG. 26A indicates the direction of movement as the probe is lowered into position.

Figure 20:
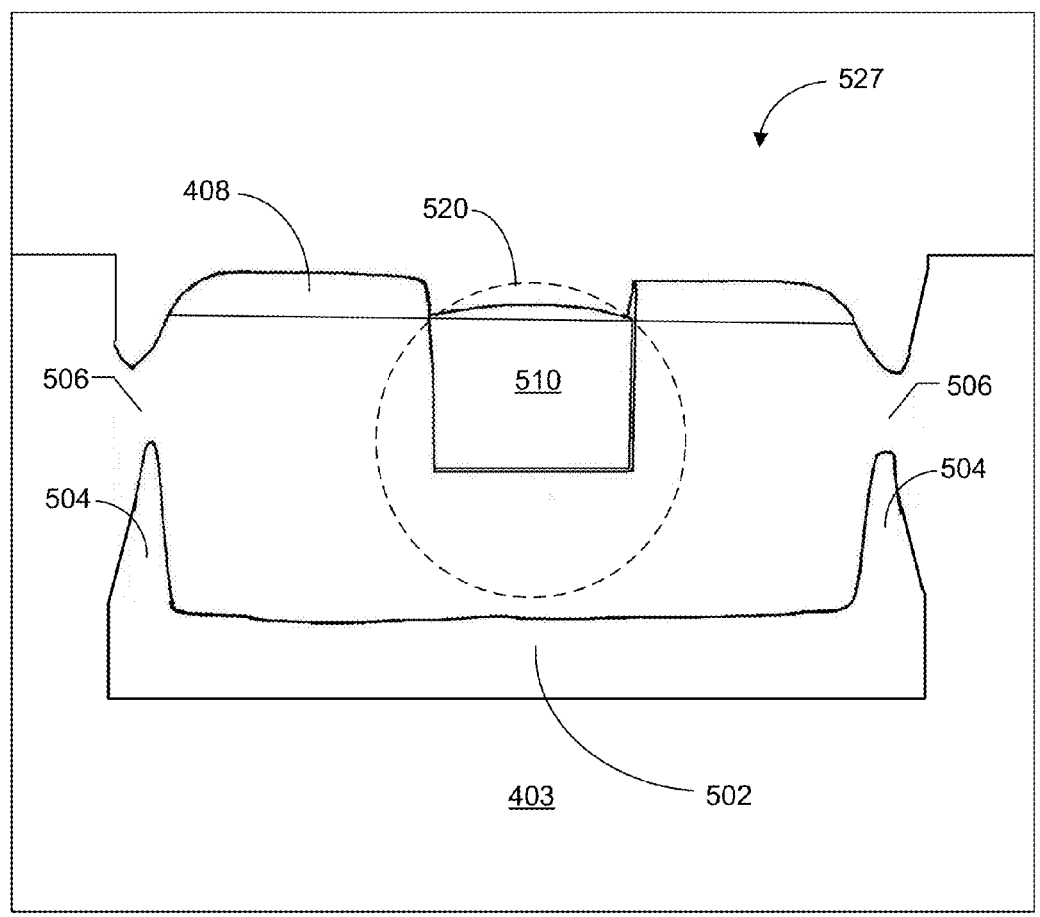
FIG. 20 shows a lamella suitable for extraction with an ex-situ sample extraction device according to the present invention.

While the probe tip should be as large as possible so that the vacuum will provide a stronger pull on the lamella, it must also be small enough to fit into the cavity in front of the sample face to a sufficient depth for the probe face to contact the side of the sample so that the sample can be drawn to the probe tip. A suitable probe contact on a sample structure according to the present invention is shown by the dashed circle 520 in FIG. 20.

Persons of ordinary skill in the art will recognize that the internal diameter of the probe will greatly affect air flow through the tube when a vacuum is applied. A larger internal diameter will allow for a more powerful vacuum. However, the internal diameter will desirably be smaller than the smallest dimension of the sample to be extracted to prevent the sample from being pulled into the probe interior. In a preferred embodiment, the probe tip has a roughened face to minimize surface contact between the sample and the probe and thus minimize any electrostatic or other attraction between the sample and the probe as discussed below.

Referring also to FIGS. 27-28, in step 708, the probe 616 is then moved toward the sample face 951 (to the position shown by dashed line 616) and a vacuum applied through the open probe tip. The arrow 922 in FIG. 27 indicates the direction of movement as the probe 616 is moved forward to make contact with the sample. Arrow 918 shows the direction of air flow when the vacuum is applied. In step 710, once the probe tip makes contact with the sample face 951, the probe 616 can be pushed slightly forward to break any remaining connection between the sample and the substrate. It may be necessary to dither the probe back and forth as shown by arrow 919 in order to completely separate the sample. The sample is held against the probe tip by a combination of electrostatic force and the vacuum pressure exerted through the probe tip. In some embodiments, the probe can be held in place by electrostatic forces alone. When vacuum pressure is used to hold the sample in place, the probe tip will preferably be adapted to minimize the electrostatic attraction between the sample and probe tip. For example, the probe tip can have a roughened face to minimize surface contact between the sample and the probe or it can be coated with a material that reduces the electrostatic attraction. Minimizing the electrostatic attraction makes it easier to release the sample and to more precisely place the sample at a desired location.

Also, in some embodiment, a probe having a conductive coating can be used to facilitate a contact sensor to determine when the probe tip is in contact with the sample. Sample contact may also be determined by using a flow sensor to monitor pressure changes in the vacuum applied through the probe tip.

Figure 29:
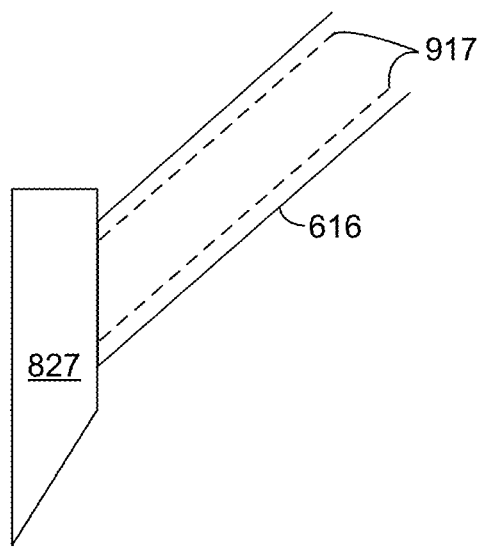
FIGS. 29-32 illustrate steps in the transfer of an extracted sample to a TEM grid according to the present invention.
Figure 30:
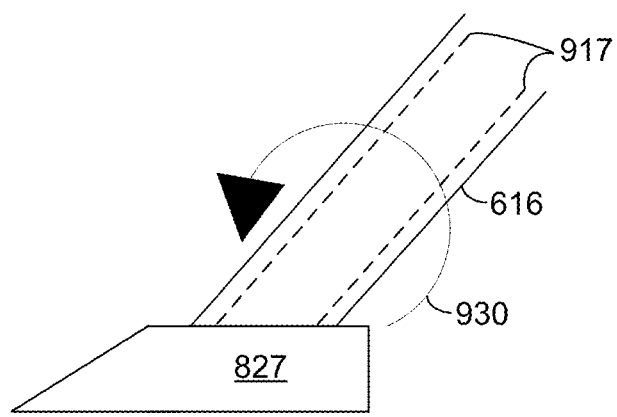

In step 712, the sample can then be lifted away from the wafer until it is safely above the substrate. As shown in FIGS. 29-30, in step 714, the probe 616 is then rotated 180 degrees, as shown by arrow 930, to place the sample in a horizontal drop-off position. After rotation, the sample face will lie in a plane parallel to the substrate surface. As discussed above, the ESP probe tip 940 is preferably beveled at an angle of approximately 45 degrees, and the entire ESP probe 616 is oriented at an approximately 45 degree angle to the sample face. This allows the beveled probe tip to be substantially parallel to the vertical sample face for sample extraction and also be substantially parallel to the horizontal support film after rotation. Skilled persons will recognize that the angle of the bevel and the angle of the entire probe can be varied. However, the sum of the two angles should typically be approximately 90 degrees where the sample has a substantially vertical face. For example, if a 60 degree bevel is used, the probe should be oriented at an angle of approximately 30 degrees (with respect to the sample face). Where angles other than 45 degrees are used, the TEM grid may have to be tilted to allow the sample to be placed flat on the TEM grid after the probe is rotated. In another preferred embodiment, the sample holder, such as a TEM grid, could be mounted vertically. In that case, rotation would not be necessary and the sample (held vertically by the probe tip) could be placed directly on the sample holder.

Figure 31:
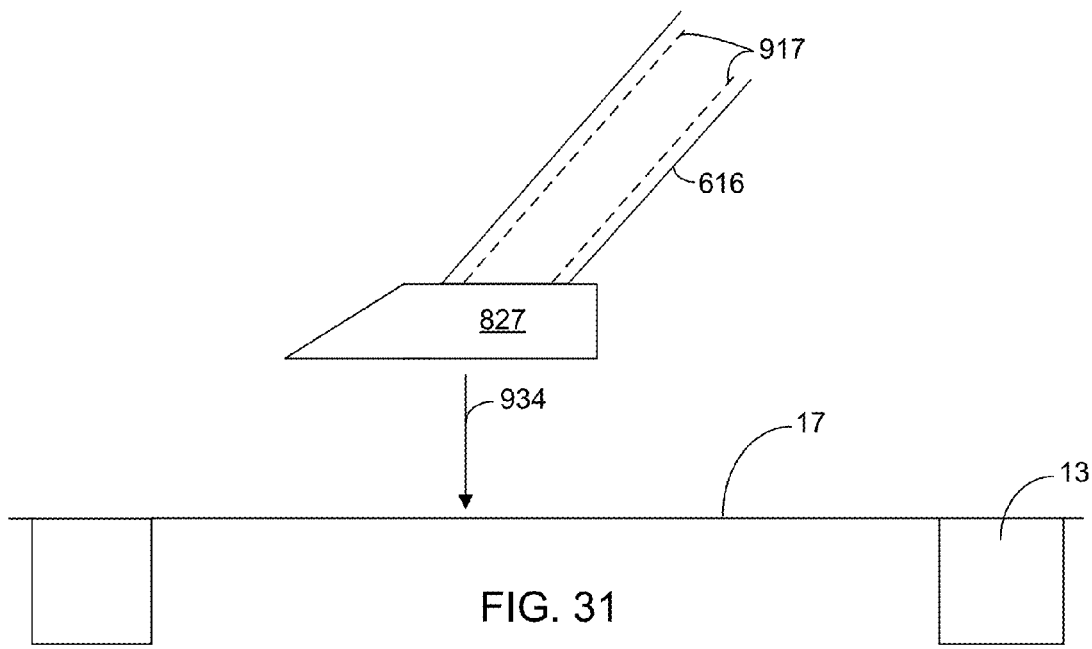
Figure 32:
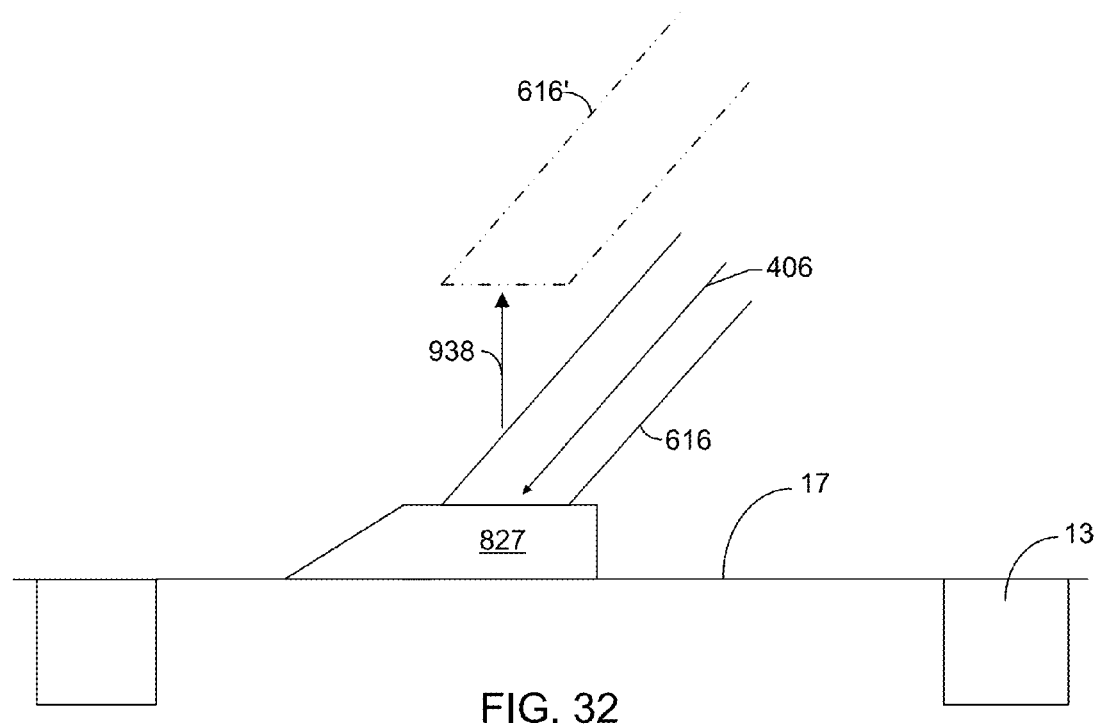

In step 716, the ESP stage is then moved so that the TEM grid holder is centered in the microscope optical field. The TEM grid holder is preferably mounted on a rotating stage so that the grid can be aligned to the XY axis of the wafer stage by rotating the TEM grid. Preferably, the stage can also be tilted if a non-45 degree bevel/probe orientation is used. The grid can also be rotated in the appropriate direction to account for orientation errors in the positioning of the sample. In step 718, the probe is positioned so that the sample is located above the desired TEM grid cell. In step 720, the probe 616 is lowered until the sample 827 comes into contact with the grid support film 17 as shown in FIGS. 31-32. Line 934 indicates the direction of movement of the probe 616 as the sample 827 is placed onto the support film 17. Contact can be determined by an appropriate contact sensor or controlled automatically based on known positions and calibration data. The particular film used for the TEM grid is preferably a film having a smooth and uniform surface. A firmer surface is better for ensuring good surface contact between the lamella and the film to facilitate the transfer and accurate placement of the lamella.

Once the sample is placed onto the TEM grid surface, in many cases the lamella will adhere to the film surface even if the vacuum through the probe tip remains turned on. In step 721, the vacuum pressure is optionally turned off to facilitate the release of the sample from the probe tip. In some embodiments, in optional step 722, the vacuum pressure can be changed to a slight over-pressure 406 in order to force the release of a sample that remains adhered to the probe tip.

The probe is then moved to a safe distance above the TEM grid in step 724 as shown in FIG. 32. Line 938 indicates the direction of movement of the probe after the sample has been released. If there are other samples to be extracted in step 726, the process described in steps 702-724 is repeated. Once all samples have been extracted, the wafer can be returned to the production line (step 728).

The present invention provides a number of significant advantages over the prior art. Using typical methods for TEM sample preparation, it takes highly trained and experienced operators approximately 3 hours to create and extract one sample lamella suitable for TEM analysis. For current in-line metrology techniques like top-down SEM or CD-SEM analysis, as many as 20 different sites across a wafer might need to be measured. Using prior art methods of TEM sample preparation, it would take about 60 hours just to prepare suitable TEM samples from 20 different sites.

Also, because so much of the TEM sample preparation must be performed manually, the process is very labor intensive and requires the use of highly skilled operators (which of course translates into high labor costs). The increased throughput and reproducibility of the TEM analysis provided by the present invention will allow TEM based metrology on objects such as integrated circuits on semiconductor wafer to be used for in-line process control. For example, TEM analysis according to the present invention could be utilized in a wafer fabrication facility to provide rapid feedback to process engineers to troubleshoot or improve processes. This kind of process control for the very small features that can only be measured by TEM is not possible using prior art TEM sample preparation methods.

Further, current manual TEM sample preparation methods produce samples having a great deal of variation. In order to use a metrology technique for process control, it is highly desirable that the samples be as uniform as possible. Because current methods require the final thinning of a TEM lamella to be manually controlled, there is an unavoidable variation in sample thickness for lamellae from different sample sites. Manual control over other key elements in the sample creation process, such as fiducial placement (which determines the actual lamella location) introduces even more variation and further reduces the precision of the final lamella preparation. The variation between samples is even greater when lamellae are prepared by different operators.

Using the present invention, however, results in a significant improvement in the TEM sample preparation process. As discussed above, preferred embodiments of the present invention have been used to create and extract S/TEM samples with a thickness in the 50-100 nm range with very minimal site-to-site variation. The process produces a lamella in roughly 18 minutes, with a site-to-site 3-sigma final lamella thickness variation of roughly 20 nm. The time required to sample 20 different sites on a wafer surface drops to about 6 hours (as opposed to 60 hours for current methods). The process is also much less labor intensive and does not require operators with as high a degree of training or experience. Because more of the process is automated, variation between lamella samples is also minimized.

The increased throughput and reproducibility of the TEM analysis provided by the present invention will allow TEM based metrology on objects such as integrated circuits on semiconductor wafer to be used for in-line process control. For example, TEM analysis according to the present invention could be utilized in a wafer fabrication facility to provide rapid feedback to process engineers to troubleshoot or improve processes. This kind of process control for the very small features that can only be measured by TEM is not possible using prior art TEM sample preparation methods.

The invention has broad applicability and can provide many benefits as described and shown in the examples above. The embodiments will vary greatly depending upon the specific application, and not every embodiment will provide all of the benefits and meet all of the objectives that are achievable by the invention. For example, in a preferred embodiment TEM lamella samples are created using a gallium liquid metal ion source to produce a beam of gallium ions focused to a sub-micrometer spot. Such focused ion beam systems are commercially available, for example, from FEI Company, the assignee of the present application. However, even though much of the previous description is directed toward the use of FIB milling, the milling beam used to process the desired TEM samples could comprise, for example, an electron beam, a laser beam, or a focused or shaped ion beam, for example, from a liquid metal ion source or a plasma ion source, or any other charged particle beam. Also, the invention described above could be used with automatic defect reviewing (ADR) techniques, which could identify defects via die-to-die or cell-to-cell ADR. A lamella containing the defect could be created and removed with or without milling fiducials. Further, although much of the previous description is directed at semiconductor wafers, the invention could be applied to any suitable substrate or surface. The steps described above are preferably performed automatically under computer control. That is, the steps are performed by the computer in accordance with programmed instructions and without human intervention. Automatic operation does not exclude a person initiating any step or the entire process.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of processing a semiconductor wafer, comprising:
    selecting a process recipe including process recipe values for a wafer, said process recipe including positional data for one or more sample sites to be analyzed;
    loading the wafer into a charged particle beam system, said charged particle beam system to process the wafer according to one or more of the selected process recipe values;
    navigating to each sample site using said positional data;
    imaging each sample site;
    based on geometric information from CAD data describing the respective sample sites, automatically determining a precise sample location of a respective target structure using image processing and metrology;
    automatically positioning and placing one or more fiducial markers at each respective sample site;
    referencing the fiducial markers while automatically milling the wafer surface on two sides of respective sample locations leaving a sample comprising a thin layer of material including at least a portion of the target structure;
    extracting the respective samples from the wafer and transferring the samples to a TEM system;
    imaging the respective samples with the TEM system according to one or more of the selected process recipe values;
    analyzing the TEM images to determine a feature dimension of the target structure.

2. The method of claim 1 wherein automatically positioning and placing one or more fiducial markers further comprises:
    identifying at least one desired first fiducial location for the respective sample sites;
    milling a combination of at least one high precision fiducial marker and one low precision fiducial marker at fixed positions with respect to the desired first fiducial locations; and
    determining edge positions for automatically milling the wafer surface with respect to said fiducial markers.

3. The method of claim 2 in which the position of the precision fiducial markers is further precisely placed around the target structure using automated metrology calipers to find the edges of the target structure.

4. The method of claim 1 further comprising adjusting the positional data or fiducial marker locations for at least one additional sample site in response to the determined dimension.

5. The method of claim 1 further comprising providing CAD data to specify the location of the one or more fiducial markers with respect to the target structure on the wafer.

6. The method of claim 1 further comprising, after imaging the samples with TEM, returning the wafer to a production line.

7. The method of claim 1 further comprising, based on the measured feature dimensions, adjusting a fabrication process on a production line to obtain a desired feature dimension for similar features.

8. The method of claim 1 wherein automatically milling the substrate surface on two sides of a desired sample comprises automatically milling the substrate surface on either side of a desired sample location leaving a thin layer of material less than 100 nm thick.

9. The method of claim 1 wherein extracting the samples from the wafer comprises automatically extracting the samples from the wafer.

10. A method of processing a semiconductor wafer, comprising:
    selecting a process recipe including process recipe values for a wafer, said process recipe including positional data for one or more sample sites to be analyzed;
    loading the wafer into a charged particle beam system, said charged particle beam system to process the wafer according to one or more of the selected process recipe values;
    navigating to each sample site using said positional data;
    imaging each sample site;
    automatically determining a precise sample location of a respective target structure using image processing and metrology;
    providing CAD data to specify the location of the one or more fiducial markers with respect to the target structure on the wafer, automatically positioning and placing one or more fiducial markers at each respective sample site;
    referencing the fiducial markers while automatically milling the wafer surface on two sides of respective sample locations leaving a sample comprising a thin layer of material including at least a portion of the target structure;
    extracting the respective samples from the wafer and transferring the samples to a TEM system;
    imaging the respective samples with the TEM system according to one or more of the selected process recipe values;
    analyzing the TEM images to determine a feature dimension of the target structure.

11. The method of claim 10 wherein automatically positioning and placing one or more fiducial markers further comprises:
    identifying at least one desired first fiducial location for the respective sample sites;
    milling a combination of at least one high precision fiducial marker and one low precision fiducial marker at fixed positions with respect to the desired first fiducial locations; and determining edge positions for automatically milling the wafer surface with respect to said fiducial markers.

12. The method of claim 11 in which the position of the precision fiducial markers is further precisely placed around the target structure using automated metrology calipers to find the edges of the target structure.

13. The method of claim 10 further comprising adjusting the positional data or fiducial marker locations for at least one additional sample site in response to the determined dimension.

14. The method of claim 10, automatically determining a precise sample location of a respective target structure using image processing and metrology is based on geometric information from CAD data describing the respective sample sites.

15. The method of claim 10 further comprising, after imaging the samples with TEM, returning the wafer to a production line for further processing.

16. The method of claim 10 further comprising, based on the measured feature dimensions, adjusting a fabrication process on a production line to obtain a desired feature dimension for similar features.

17. The method of claim 10 wherein automatically milling the substrate surface on two sides of a desired sample comprises automatically milling the substrate surface on either side of a desired sample location leaving a thin layer of material less than 100 nm thick.

18. The method of claim 10 wherein extracting the samples from the wafer comprises automatically extracting the samples from the wafer.

* * * * *